United States Patent [19]

Ichijima et al.

[11] Patent Number: 4,477,563
[45] Date of Patent: Oct. 16, 1984

[54] SILVER HALIDE COLOR PHOTOGRAPHIC LIGHT-SENSITIVE MATERIAL

[75] Inventors: Seiji Ichijima; Kei Sakanoue; Hidetoshi Kobayashi; Keiichi Adachi, all of Kanagawa, Japan

[73] Assignee: Fuji Photo Film Co., Ltd., Kanagawa, Japan

[21] Appl. No.: 526,314

[22] Filed: Aug. 25, 1983

Related U.S. Application Data

[63] Continuation-in-part of Ser. No. 358,723, Mar. 16, 1982, abandoned.

[30] Foreign Application Priority Data

Mar. 16, 1981 [JP] Japan .................................. 56-37374

[51] Int. Cl.$^3$ ............................................... G03C 7/26
[52] U.S. Cl. .................................... 430/544; 430/553; 430/555; 430/557; 430/558; 430/957
[58] Field of Search ............... 430/544, 553, 555, 557, 430/558, 957

[56] References Cited

U.S. PATENT DOCUMENTS 3,617,291 11/1971 Sawdey ............................. 430/957
3,700,457 10/1972 Youngquist ....................... 430/957
4,149,886 4/1979 Tanaka et al. ..................... 430/382
4,170,479 10/1979 Usami ................................ 430/957
4,187,110 2/1980 Yagihara et al. ................... 430/544
4,256,881 3/1981 Simons et al. ..................... 430/544
4,286,054 8/1981 Englemann et al. ............... 430/544

Primary Examiner—J. Travis Brown
Attorney, Agent, or Firm—Sughrue, Mion, Zinn, Macpeak, and Seas

[57] ABSTRACT

A silver halide color photographic light-sensitive material is described comprising a support having thereon a silver halide emulsion layer containing a coupler having, at the coupling active position, a group which provides a compound having a development inhibiting property when the group is released from the coupling device position of the coupler upon the color development reaction and which is decomposed to a compound which does not substantially influence the photographic properties when the compound diffuses into a color developing solution.

The silver halide color photographic light-sensitive material containing a novel class of development inhibitor releasing couplers provides color images of good sharpness and improved color reproduction without causing contamination of the processing solution.

22 Claims, No Drawings

SILVER HALIDE COLOR PHOTOGRAPHIC LIGHT-SENSITIVE MATERIAL

STATUS OF RELATED APPLICATIONS

This is a continuation-in-part of application Ser. No. 358,723, filed Mar. 16, 1982, now abandoned.

BACKGROUND OF THE INVENTION

The present invention relates to a color photographic light-sensitive material containing a photographic coupler, and more particularly a novel development inhibitor releasing coupler capable of releasing a development inhibitor upon the reaction with the oxidation product of a developing agent (hereinafter referred to as a DIR coupler).

It is well known that, by the color development of a silver halide color photographic light-sensitive material, an oxidized aromatic primary amine type color developing agent is reacted with a coupler to form a dye, such as an indophenol, an indoaniline, an indamine, an azomethine, a phenoxazine, a phenazine, and the like, thus forming a color image. In this type, the subtractive color process is ordinarily used for color reproduction, i.e., silver halide emulsions selectively sensitive to blue, green, and red light, and yellow, magenta, and cyan color image forming materials which are respectively present therein form the complementary color thereof. For example, a coupler of the acylacetanilide or dibenzoylmethane type is used for forming a yellow color image; a coupler of the pyrazolone, pyrazolobenzimidazole, cyanoacetophenone or indazolone type is used for forming a magenta color image; and a coupler of the phenol type, such as a phenol or a naphthol, is used for forming a cyan color image.

The color photographic light-sensitive material is usually developed by one of two main processes, i.e., a coupler-in-developer type process in which a coupler is employed to add to a developing agent and a coupler-incorporated type process in which a coupler is employed to incorporate into each light-sensitive layer of the light-sensitive material so as to maintain its independent function. In the latter process, a coupler for forming a color image is added to a silver halide emulsion. A coupler to be added to a silver halide emulsion is required to render the coupler non-diffusible (diffusion resistant) in a binder matrix of the emulsion.

It is also known that a compound capable of releasing a development inhibitor depending on the density of the image during development is incorporated into a photographic light-sensitive material. In general, such a type of compound is reacted with the oxidation product of a color developing agent to release a development inhibitor. As a typical example, the so-called DIR coupler has been known in which a group having a development inhibiting function when released from the active position is introduced at the coupling position of the coupler. Examples of the DIR couplers include the compounds as described in U.S. Pat. Nos. 3,227,554, 3,701,783, 3,615,506, 3,617,291, etc., and the further improved compounds are described in Japanese Patent Publication No. 34933/80. The DIR couplers are used for the purpose of improving the sharpness of a color image due to the edge effects and the color reproducibility due to the interlayer effects, etc., as well known from the description of the above described patents.

These known DIR couplers are efficient to a certain extent. However, it has been desired to further improve their properties. In particular, known DIR couplers have the disadvantage that development inhibitor which is released during the color development diffuses from the light-sensitive material into a processing solution and accumulates in the processing solution, which, as the result, exhibits a development inhibiting function. This results in finding it difficult to constantly obtain a determined gradation in a method in which a large amount of light-sensitive materials are processed continuously, for example, in a conventional processing method commercially carried out. Thus, the contamination of processing solution arising from the development inhibitors released from the DIR couplers has been a serious problem.

In order to overcome this problem, expedient counterplans have been conducted but these have some disadvantages, and thus a satisfactory solution to this problem has not been known. For instance, there is a method in which the amount of DIR coupler employed is restricted, a method in which a color developing solution is frequently exchanged with a fresh color developing solution, a method in which development inhibitor diffusing out from the light-sensitive layer is captured by a fine grain emulsion layer which is additionally provided in the light-sensitive material, and the like. However, these method are accompanied with disadvantages in which the improvement in photographic properties due to the DIR couplers decreases, in that the cost increases remarkably, and the like.

Further, DIR couplers having an ethoxycarbonyl-substituted-2-benzotriazolyl group are known as described in U.S. Pat. No. 3,617,291. However, these DIR couplers have an unsatisfactory decomposition speed and improvement in this respect is desired.

SUMMARY OF THE INVENTION

Therefore, an object of the present invention is to provide a color photographic light-sensitive material having good sharpness in a color image by the use of a novel DIR coupler.

Another object of the present invention is to provide a color photographic light-sensitive material of improved color reproducibility by the use of a novel DIR coupler.

Still another object of the present invention is to provide a color photographic light-sensitive material which does not contaminate a color developing solution and is suitable for use in a processing method in which a color developing solution is employed continuously and repeatedly by the use of a novel DIR coupler.

Other objects of the present invention will become apparent from the following detailed description and examples.

These objects of the present invention are attained by a silver halide color photographic light-sensitive material comprising a support having thereon a silver halide emulsion layer containing a coupler having, at the coupling active position, a group which provides a compound having a development inhibiting property when the group is released from the coupling active position of the coupler upon the color development reaction and which is decomposed to a compound which does not substantially influence the photographic properties after when the compound diffuses out into a color developing solution.

DETAILED DESCRIPTION OF THE INVENTION

A coupler used according to the present invention is characterized in that upon the coupling reaction with an oxidation product of a color developing solution, it releases a releasable group attached to the coupling position thereof which provides a compound having the development inhibiting function, and the compound having the development inhibiting function is decomposed to a compound which does not substantially influence the photographic properties after diffusing out into a color developing solution. By the use of the coupler according to the present invention the above described problems are essentially overcome.

The coupler used according to the present invention is a DIR coupler, and can be represented by formula (I)

$$A-L_1)_a Z-L_2-Y)_b \qquad (I)$$

wherein A represents a coupler component; Z represents an essential portion of a compound having a development inhibiting function which is bonded to the coupling position of the coupler directly (when a is 0) or through a connecting group of the formula $L_1$ (when a is 1); Y represents a substituent for revealing the development inhibiting function of Z and is bonded to Z through a connecting group of the formula $L_2$; $L_2$ represents a connecting group containing a chemical bond which is broken in a developing solution; a represents 0 or 1; and b represents 1 or 2, and when b is 2, the groups represented by $-L_2$-Y may be the same or different.

The compound represented by formula (I) releases a compound of the formula $^{\ominus}Z-L_2-Y)_b$ or $^{\ominus}L_1-Z-L_2-Y)_b$ after coupling with an oxidation product of a color developing agent. In the compound of the formula $^{\ominus}L_1-Z-L_2-Y)_b$, $L_1$ immediately breaks-off to form a compound of the formula $^{\ominus}Z-L_2-Y)_b$. The compound of the formula $^{\ominus}Z-L_2-Y)_b$ diffuses through a light-sensitive layer while exhibiting the development inhibiting function, and a part of it diffuses out into the color development processing solution. The compound of the formula $^{\ominus}Z-L_2-Y)_b$ diffusing out into the processing solution is rapidly decomposed at a chemical bond of $L_2$. That is, the connection between Z and Y is broken and a compound having only a small development inhibiting function in which a water-soluble group is attached to Z remains in the developing solution, and thus the development inhibiting function substantially disappears. Consequently, the compounds having the development inhibiting function are not accumulated in the processing solution and thus it is possible to repeatedly utilize the processing solution. In addition, it is possible to incorporate a sufficient amount of DIR coupler into the light-sensitive material.

As a yellow color image forming coupler residue represented by A, there are illustrated, for example, a coupler residue of a pivaloylacetanilide type, a benzoylacetanilide type, a malondiester type, a malondiamide type, a dibenzoylmethane type, a benzothiazolylacetamide type, a malonester monoamide type, a benothiazolylacetate type, a benzoxazolylacetamide type, a benzoxazolylacetate type, a malondiester type, a benzimidazolylacetamide type or a benzimidazolylacetate type, a coupler residue derived from a hetero ring substituted acetamide or a hetero ring substituted acetate as described in U.S. Pat. No. 3,841,880, a coupler residue derived from an acylacetamide as described in U.S. Pat. No. 3,770,446, British Pat. No. 1,459,171, West German Patent Application (OLS) No. 2,503,099, Japanese Patent Application (OPI) No. 139738/75 (the term "OPI" as used herein refers to a "published unexamined Japanese patent application") or Research Disclosure, No. 15737, a heterocyclic type coupler residue as described in U.S. Pat. No. 4,046,574, or the like.

As a magenta color image forming coupler residue represented by A, a coupler residue containing a 5-oxo-2-pyrazoline nucleus, a pyrazolo-[1,5-a]-benzimidazole nucleus or a cyanoacetophenone type coupler residue is preferred.

As a cyan color image forming coupler residue represented by A, a coupler residue containing a phenol nucleus or an α-naphthol nucleus is preferred.

Furthermore, a coupler which releases a development inhibitor upon the coupling with an oxidation product of a developing agent and does not substantially form a dye also has the effect of a DIR coupler. As a coupler residue of such a type represented by A, there are illustrated, for example, a coupler residue as described in U.S. Pat. Nos. 4,052,213, 4,088,491, 3,632,345, 3,958,993 and 3,961,959, or the like.

As the essential portion of a development inhibitor represented by Z, there are illustrated a divalent heterocyclic group or a divalent heterocyclic thio group. Examples of the groups are set forth below together with the position at which the group of the formula $A-L_1)_a$ is bonded and the position at which the group of the formula $-L_2-Y)_b$ is bonded.

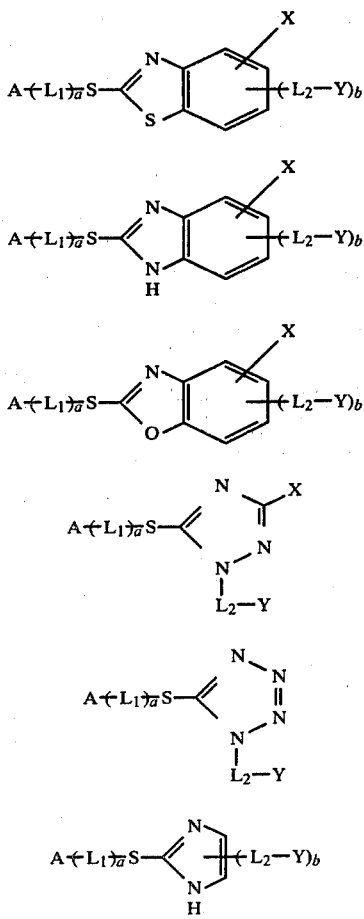

-continued

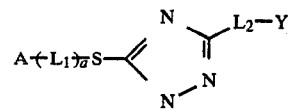

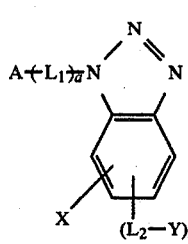

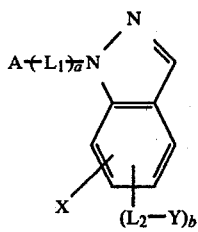

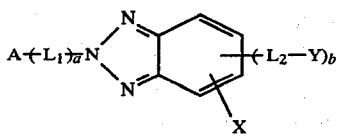

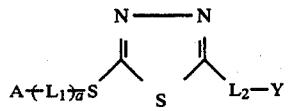

In the above formulae, a substituent represented by X, which is included in the portion represented by Z in formula (I), is a hydrogen atom, a halogen atom, an alkyl group, an alkenyl group, an alkanamido group, an alkenamido group, an alkoxy group, a sulfonamido group, or an aryl group.

Examples of the group represented by Y in formula (I) include, for example, a substituted straight chain or substituted branched chain alkyl group, a cyclic alkyl group which is unsubstituted or substituted, an alkenyl group, an aryl group, an aralkyl group or a heterocyclic group.

Examples of the connecting group represented by $L_1$ in formula (I) include, for example, the following groups which are shown together with A and $Z—L_2-Y)_b$.

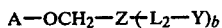

the connecting group described in U.S. Pat. No. 4,146,396

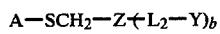

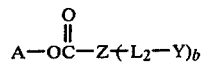

the connecting group described in West German Patent Application (OLS) No. 2,626,315

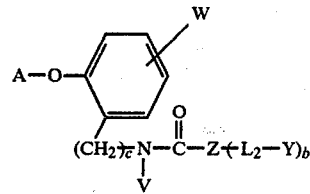

wherein W has the same meaning as defined hereinafter, V represents a hydrogen atom or an alkyl group having 1 to 10 carbon atoms, and c is 0 or an integer of 1 to 2, the connecting group described in West German Patent Application (OLS) No. 2,855,697.

In the case of these DIR couplers (i.e., wherein a is 1 in formula (I)), a group released from the coupler upon the reaction with an oxidation product of a developing agent is immediately decomposed to release a development inhibitor of the formula $H-Z—L_2-Y)_b$. Therefore, these DIR couplers which do not have a group represented by $L_1$ (i.e., those wherein a is 0 in formula (I)) have the same effects as the present invention.

The connecting group represented by $L_2$ in the formula (I) contains a chemical bond which is broken in a developing solution. Examples of the chemical bonds include those shown in the table below. These chemical bonds are broken with a nucleophilic agent such as a hydroxy ion or hydroxylamine, etc., which is a component of the color developing solution, and thus the effects according to the present invention are achieved.

| Chemical Bond Included in L | Reaction which Breaks Chemical Bond (Reaction with $^-OH$) |
| --- | --- |
| —COO— | —COOH + HO— |
| H<br>—NCOO— | —NH$_2$ + HO— |
| —SO$_2$O—<br>—OCH$_2$CH$_2$SO$_2$— | —SO$_3$H + HO—<br>—OH + CH$_2$ = CHSO$_2$— |
| —OCO—<br>‖<br>O | —OH + HO— |
| —NHCCO—<br>‖‖<br>OO | —NH$_2$ + HO— |

The chemical bonds shown in the above table are connected on one side to Z directly or through an alkylene group and/or a phenylene group, and on the other side to Y directly. When the chemical bond is connected to Z through an alkylene group or a phenylene group, an ether bond, an amido bond, a carbonyl group, a thioether bond, a sulfone group, a sulfonamido bond, and a urea bond may be contained in these divalent groups.

Preferred examples of the connecting groups represented by L are set forth below together with the position at which Z is bonded and the position at which Y is bonded.

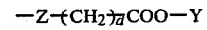

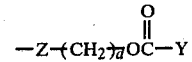

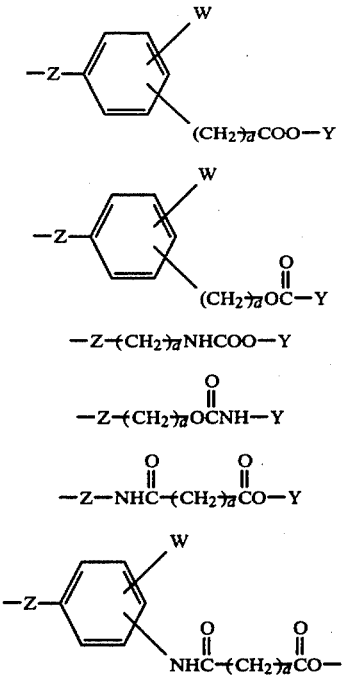

In the above formulae, d represents 0 or an integer of 1 to 10, and preferably 0 or an integer of 1 to 5; W represents a hydrogen atom, a halogen atom, an alkyl group having from 1 to 10 carbon atoms, and preferably from 1 to 5 carbon atoms, an alkanamido group having from 1 to 10 carbon atoms, and preferably from 1 to 5 carbon atoms, an alkoxy group having from 1 to 10 carbon atoms, and preferably from 1 to 5 carbon atoms, an alkoxycarbonyl group having from 1 to 10 carbon atoms, and preferably from 1 to 5 carbon atoms, an aryloxycarbonyl group, an alkanesulfonamido group having from 1 to 10 carbon atoms, and preferably from 1 to 5 carbon atoms, an aryl group, a carbamoyl group, an N-alkylcarbamoyl group having from 1 to 10 carbon atoms, and preferably from 1 to 5 carbon atoms, a nitro group, a cyano group, an arylsulfonamido group, a sulfamoyl group, an imido group, or the like.

The alkyl group or the alkenyl group represented by X or the alkenyl group represented by Y represents, in more detail, a straight chain, branched chain or cyclic alkyl group or alkenyl group having from 1 to 10 carbon atoms, and preferably from 1 to 5 carbon atoms, and which may be substituted; and the alkyl group represented by Y represents, in more detail, a straight chain or branched chain alkyl group having from 1 to 10 carbon atoms, and preferably from 1 to 5 carbon atoms, which is substituted, or a cyclic alkyl group having from 3 to 10 carbon atoms, and preferably from 3 to 6 carbon atoms, which may be substituted. Examples of the substituents include, for example, a halogen atom, a nitro group, an alkoxy group having from 1 to 4 carbon atoms, an aryloxy group having from 6 to 10 carbon atoms, an alkanesulfonyl group having from 1 to 4 carbon atoms, an arylsulfonyl group having from 6 to 10 carbon atoms, an alkanamido group having from 1 to 5 carbon atoms, an anilino group, a benzamido group, an alkylcarbamoyl group having from 1 to 6 carbon atoms, a carbamoyl group, an arylcarbamoyl group having from 6 to 10 carbon atoms, an alkylsulfonamido group having 1 to 4 carbon atoms, an arylsulfonamido group having from 6 to 10 carbon atoms, an alkylthio group having from 1 to 4 carbon atoms, an arylthio group having from 6 to 10 carbon atoms, a phthalimido group, a succinimido group, an imidazolyl group, a 1,2,4-triazolyl group, a pyrazolyl group, a benzotriazolyl group, a furyl group, a benzothiazolyl group, an alkylamino group having from 1 to 4 carbon atoms, an alkanoyl group having from 1 to 4 carbon atoms, a benzoyl group, an alkanoyloxy group having from 1 to 4 carbon atoms, a benzoyloxy group, a perfluoroalkyl group having from 1 to 4 carbon atoms, a cyano group, a tetrazolyl group, a hydroxy group, a carboxy group, a mercapto group, a sulfo group, an amino group, an alkylsulfamoyl group having from 1 to 4 carbon atoms, an arylsulfamoyl group having from 6 to 10 carbon atoms, a morpholino group, an aryl group having from 6 to 10 carbon atoms, a pyrrolidinyl group, a ureido group, a urethane group, an alkoxycarbonyl group having from 1 to 6 carbon atoms, an aryloxycarbonyl group having from 6 to 10 carbon atoms, an imidazolidinyl group, an alkylidenamino group having from 1 to 6 carbon atoms.

The alkanamido group or the alkenamido group represented by X represents in detail a straight chain, branched chain, or cyclic alkanamido group or alkenamido group having 1 to 10 carbon atoms, preferably 1 to 5 carbon atoms and which may be substituted. Examples of the substituents are selected from the substituent illustrated with respect to the alkyl group or alkenyl group described above.

The alkoxy group represented by X represents, in more detail, a straight chain, branched chain or cyclic alkoxy group having from 1 to 10 carbon atoms, and preferably from 1 to 5 carbon atoms, and may be substituted. Examples of the substituents are selected from the substituents illustrated with respect to the alkyl group or alkenyl group described above.

The aryl group represented by Y includes a phenyl group or a naphthyl group and which may be substituted. Examples of the substituents are selected from the substituents illustrated with respect to the alkyl group or alkenyl group described above and an alkyl group having from 1 to 4 carbon atoms.

The heterocyclic group represented by Y includes a diazolyl group (e.g., a 2-imidazolyl group, a 4-pyrazolyl group, etc.), a triazolyl group (e.g., a 1,2,4-triazol-3-yl group, etc.), a thiazolyl group (e.g., a 2-benzothiazolyl group, etc.), an oxazolyl group (e.g., a 1,3-oxazol-2-yl group, etc.), a pyrrolyl group, a pyridyl group, a diazinyl group (e.g., a 1,4-diazin-2-yl group, etc.), a triazinyl group (e.g., a 1,2,4-triazin-5-yl group, etc.), a furyl group, a diazolinyl group (e.g., an imidazolin-2-yl group, etc.), a pyrrolinyl group, a thienyl group, and the like.

Of the couplers represented by formula (I), those represented by formula (II), (III), or (IV) described below are useful. These couplers are preferred because the development inhibiting function of the released group just after releasing is strong.

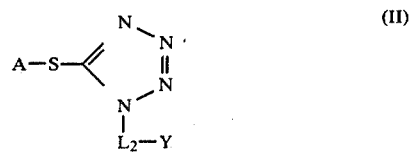

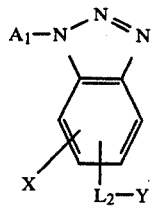 (III)

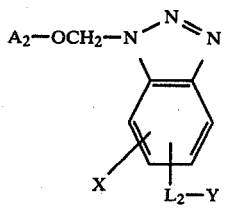 (IV)

In formula (II), A, $L_2$ and Y each has the same meaning as defined for formula (I).

In formula (III), $A_1$ represents a yellow coupler residue, a magenta coupler residue or a substantially non-color forming coupler residue same as defined for formula (I).

In formula (IV), $A_2$ represents a cyan coupler residue same as defined for formula (I).

In formulae (III) and (IV), X, $L_2$ and Y each has the same meaning as defined for formula (I).

Furthermore, couplers represented by formula (V), (VI), (VII), (VIII), (IX), (X), or (XI) particularly exhibit the effects according to the present invention. These couplers are preferred because of their high coupling releasing speeds.

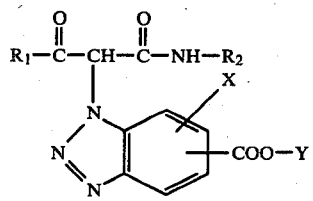 (V)

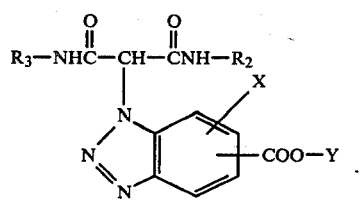 (VI)

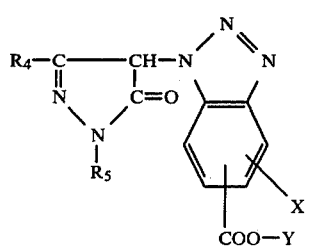 (VII)

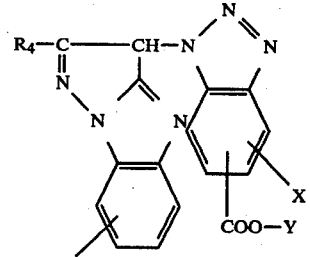 (VIII)

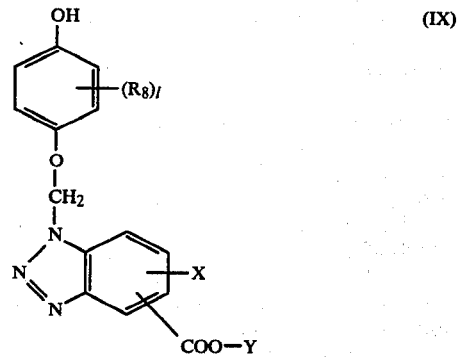 (IX)

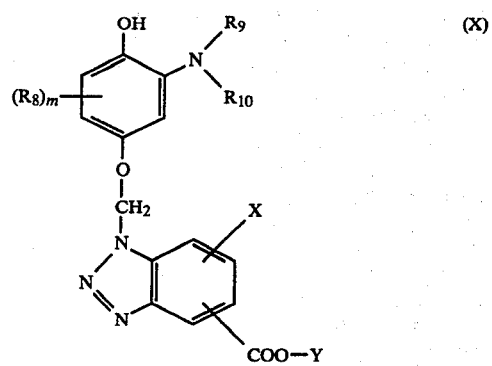 (X)

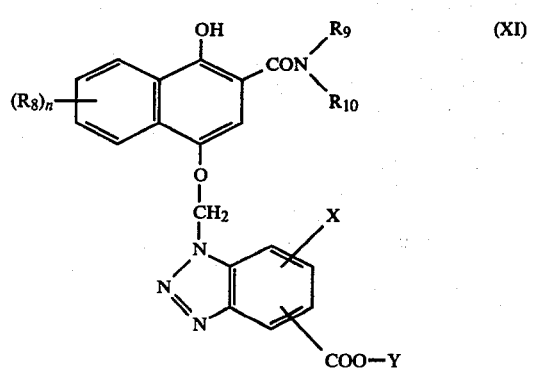 (XI)

In formulae (V) to (XI), X and Y each has the same meaning as defined for formulae (II) and (III).

In formulae (V) and (VI), $R_1$ represents an aliphatic group, an aromatic group, an alkoxy group or a heterocyclic group; and $R_2$ and $R_3$ represents an aromatic group or a heterocyclic group. The aliphatic group represented by $R_1$ has preferably from 1 to 22 carbon atoms and may be a substituted or unsubstituted aliphatic group or further a chain or cyclic aliphatic group. Preferred examples of the substituents of the alkyl group include, for example, an alkoxy group, an aryloxy group, an amino group, an acylamino group, a halogen atom, etc., and such a substituent itself may also have a substituent. Practical examples of the useful aliphatic groups represented by $R_1$ are an isopropyl group, an isobutyl group, a tertbutyl group, an isoamyl group, a tert-amyl group, a 1,1-dimethylbutyl group, a 1,1-dimethylhexyl group, a 1,1-diethylhexyl group, a dodecyl group, a hexadecyl group, an octadecyl group, a cyclohexyl group, a 2-methoxyisopropyl group, a 2-phenoxyisopropyl group, a 2-p-tertbutylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc.

The aromatic group (particularly a phenyl group) represented by $R_1$, $R_2$, or $R_3$ may be substituted. In more detail, the aromatic group such as a phenyl group represented by $R_1$, $R_2$, or $R_3$ may be substituted by a group having not more than 32 carbon atoms, e.g., an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, an alkyl-substituted succinimido group, etc., and in this case, the alkyl group may contain an aromatic group such as a phenylene group in the chain. Furthermore, the phenyl group represented by $R_1$, $R_2$, or $R_3$ may be substituted by an aryloxy group, an aryloxycarbonyl group, an arylcarbamoyl group, an arylamido group, an arylsulfamoyl group, an arylsulfonamido group, an arylureido group, etc., and the aryl moiety of these substituents may be further substituted by at least an alkyl group having from 1 to 22 carbon atoms.

The phenyl group represented by $R_1$, $R_2$, or $R_3$ may also be substituted by an amino group including an amino group substituted with a lower alkyl group having from 1 to 6 carbon atoms, a hydroxy group, a carboxy group, a sulfo group, a nitro group, a cyano group, a thiocyano group, or a halogen atom.

Also, the phenyl group represented by $R_1$, $R_2$, or $R_3$ may be condensed with another ring, for example, a naphthyl group, a quinolyl group, an isoquinolyl group, a chromanyl group, a coumaranyl group, a tetrahydronaphthyl group, etc. These substituents per se may also be substituted.

When $R_1$ represents an alkoxy group, an alkyl moiety contained in the alkoxy group represents a straight chain or branched chain alkyl group having 1 to 40 carbon atoms, and preferably from 1 to 22 carbon atoms, an alkenyl group, a cyclic alkyl group or a cyclic alkenyl group, and these groups may be substituted with a halogen atom, an aryl group, an alkoxy group, etc.

When $R_1$, $R_2$, or $R_3$ is a heterocyclic group, the heterocyclic group is bonded to a carbon atom of the carbonyl group of an α-acylacetamido group or the nitrogen atom of an amido group through one carbon atom constituting the heterocyclic ring. Examples of these heterocyclic rings include thiophene, furan, pyrane, pyrrole, pyrazole, pyridine, pyrazine, pyrimidine, pyridazine, indolizine, imidazole, thiazole, oxazole, triazine, thiadiazine, oxazine, etc. They may further have a substituent on the ring.

$R_5$ in formula (VII) represents a straight chain or branched chain alkyl group having from 1 to 40 carbon atoms, and preferably from 1 to 22 carbon atoms (e.g., a methyl group, an isopropyl group, a tert-butyl group, a hexyl group, a dodecyl group, etc.), an alkenyl group (e.g., an allyl group, etc.), a cyclic alkyl group (e.g., a cyclopentyl group, a cyclohexyl group, a norbornyl group, etc.), an aralkyl group (e.g., a benzyl group, a β-phenylethyl group, etc.), or a cyclic alkenyl group (e.g., a cyclopentenyl group, a cyclohexenyl group, etc.), and these groups may be substituted by a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, a mercapto group, etc.

Furthermore, $R_5$ may represent an aryl group (e.g., a phenyl group, an α- or β-naphthyl group, etc.). The aryl group may contain one or more substituents such as an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic group, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group, a mercapto group, etc. Preferred examples of the group represented by $R_5$ are a phenol group substituted at at least the ortho position thereof by an alkyl group, an alkoxy group, a halogen atom, etc., and such a group is useful since the coloring of the coupler remaining in a layer of a photographic film by light or heat is low.

Furthermore, $R_5$ may represent a heterocyclic group such as a 5-membered or 6-membered heterocyclic group containing a nitrogen atom, an oxygen atom, or a sulfur atom as the hetero atom or a condensed heterocyclic group such as a pyridyl group, a quinolyl group, a furyl group, a benzothiazolyl group, an oxazolyl group, an imidazolyl group, a naphthoxazolyl group, etc., a heterocyclic group substituted by a substituent such as illustrated above in regard to the aryl group $R_5$, an aliphatic acyl group, an aromatic acyl group, an alkylsulfonyl group, an arylsulfonyl group, an alkylcarbamoyl group, an arylcarbamoyl group, an alkylthiocarbamoyl group or an arylthiocarbamoyl group.

$R_4$ in formulae (VII) and (VIII) represents a hydrogen atom, a straight chain or branched chain alkyl group having from 1 to 40 carbon atoms, and preferably from 1 to 22 carbon atoms, an alkenyl group, a cyclic alkyl group, an aralkyl group, a cyclic alkenyl group (these groups may be substituted by a substituent such as illustrated above in regard to $R_5$), an aryl group, a heterocyclic group (these groups may be substituted with a substituent such as illustrated above in regard to $R_5$), an alkoxycarbonyl group (e.g., a methoxycarbonyl group, an ethoxycarbonyl group, a stearyloxycarbonyl group, etc.), an aryloxycarbonyl group (e.g., a phenoxycarbonyl group, a naphthoxycarbonyl group, etc.), an aralkyloxycarbonyl group (e.g., a benzyloxycarbonyl group, etc.), an alkoxy group (e.g., a methoxy group, an ethoxy group, a heptadecyloxy group, etc.), an aryloxy group (e.g., a phenoxy group, a tolyloxy group, etc.), an alkylthio group (e.g., an ethylthio group, a dodecylthio group, etc.), an arylthio group (e.g., a phenylthio group, an α-naphthylthio group, etc.), a carboxy group, an acylamino group (e.g., an acetylamino group, a 3-[(2,4-di-tert-amylphenoxy)acetamido]benzamido group, etc.), a diacylamino group, an N-alkylacylamino group (e.g., an N-methylpropionamido group, etc.), an N-arylacylamino group (e.g., an N-phenylacetamido group, etc.), a ureido group (e.g., a ureido group, an N-arylureido group, an N-alkylureido group, etc.), a urethane group, a thiourethane group, an arylamino group (e.g., a phenylamino group, an N-methylanilino group, a diphenylamino group, an N-acetylanilino group, a 2-chloro-5-tetradecanamidoanilino group, etc.), an alkylamino group (e.g., an n-butylamino group, a methylamino group, a cyclohexylamino group, etc.), a cycloamino group (e.g., a piperidino group, a pyrrolidino group, etc.), a heterocyclic amino group (e.g., a 4-pyridylamino group, a 2-benzoxazolylamino group, etc.), an alkylcarbonyl group (e.g., a methylcarbonyl group, etc.), an arylcarbonyl group (e.g., a phenylcarbonyl group, etc.), a sulfonamido group (e.g., an alkylsulfonamido group, an arylsulfonamido group etc.), a carbamoyl group (e.g., an ethylcarbamoyl group, a dimethylcarbamoyl group, an N-methylphenylcarbamoyl group, an N-phenylcarbamoyl group, etc.), a sulfamoyl group (e.g., an N-alkylsulfamoyl group, an N,N-dialkylsulfamoyl group, an N-arylsulfamoyl group, an N-alkyl-N-arylsulfamoyl group, an N,N-diarylsulfamoyl group, etc.), a cyano group, a hydroxy group, a mercapto group, a halogen atom, or a sulfo group.

$R_7$ in formula (VIII) represents a hydrogen atom, a straight chain or branched chain alkyl group having from 1 to 32 carbon atoms, and preferably from 1 to 22 carbon atoms, an alkenyl group, a cyclic alkyl group, an aralkyl group, or a cyclic alkenyl group, and these groups may have the substituent as illustrated above in regard to $R_5$. Also, $R_7$ may represent an aryl group or a heterocyclic group and these groups may have the substituent as illustrated above in regard to $R_5$. Further, $R_7$ may represent a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, or a mercapto group.

$R_8$, $R_9$ and $R_{10}$ in formulae (IX), (X), and (XI) each represents a group conventionally used in 4-equivalent phenol or naphthol couplers. More specifically, $R_8$ represents a hydrogen atom, a halogen atom, an aliphatic hydrocarbon residue, an acylamino group, an —O—$R_{11}$ group, or an —S—$R_{11}$ group wherein $R_{11}$ represents an aliphatic hydrocarbon residue and when two or more $R_8$ are present in one molecule, the $R_8$ groups may be different and the aliphatic hydrocarbon residue may be substituted.

$R_9$ and $R_{10}$ in formulae (X) and (XI) may represent an aliphatic hydrocarbon residue, an aryl group or a heterocyclic residue or one of $R_9$ and $R_{10}$ may be a hydrogen atom. Furthermore, the above-described group or residue may be substituted. Also, $R_9$ and $R_{10}$ may combine with each other to form a nitrogen-containing heterocyclic nucleus.

Also, l in formula (IX) is an integer of 1 to 4, m in formula (X) is an integer of 1 to 3, and n in formula (XI) is an integer of 1 to 5.

The aliphatic hydrocarbon residue indicated for $R_9$ and $R_{10}$ above may be a saturated or unsaturated or straight chain, branched chain or cyclic. A preferred aliphatic hydrocarbon residue represented by $R_9$ and $R_{10}$ is an alkyl group (e.g., a methyl group, an ethyl group, a propyl group, an isopropyl group, a butyl group, a t-butyl group, an isobutyl group, a dodecyl group, an octadecyl group, a cyclobutyl group, a cyclohexyl group, etc.) or an alkenyl group (e.g., an allyl group, an octenyl group, etc.). Typical examples of the aryl group represented by $R_9$ and $R_{10}$ are a phenyl group, a naphthyl group, etc., and typical examples of the heterocyclic residue are a pyridinyl group, a quinolyl group, a thienyl group, a piperidyl group, an imidazolyl group, etc.

As indicated above these aliphatic hydrocarbon residue, aryl group, and heterocyclic residue may be substituted such as by a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group, a morpholino group, etc.

Also, one of $R_1$, $R_2$, $R_3$, $R_4$, $R_5$, $R_7$, $R_8$, $R_9$ and $R_{10}$ of the coupler residues represented by formulae (V) to (XI) may be bonded each other or a divalent group, which combines with a divalent group of another coupler residue represented by any one of the formulae (V) to (XI) to form a symmetric or asymmetric bis-type coupler.

The following compounds are set forth as examples of the couplers used in the present invention. However, the present invention should not be construed as being limited thereto.

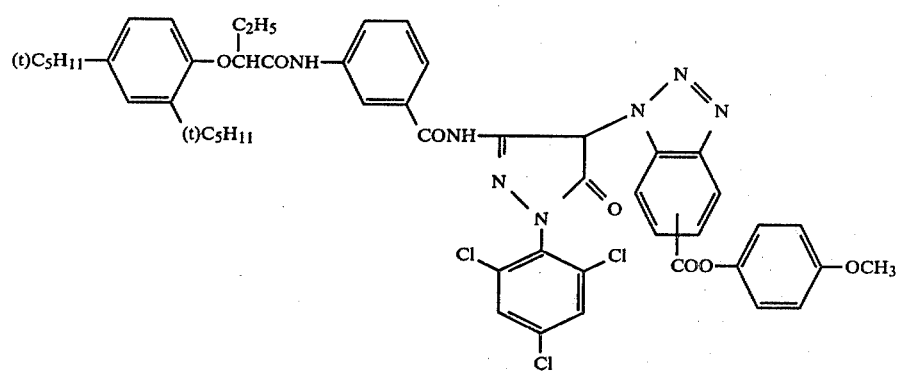
(1)
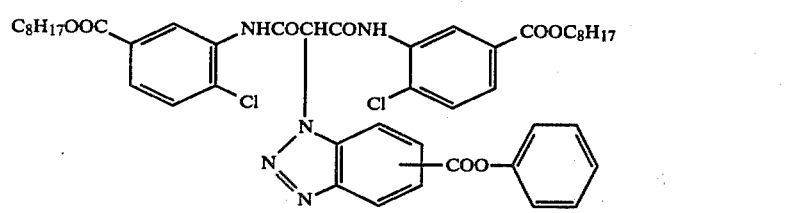
(2)
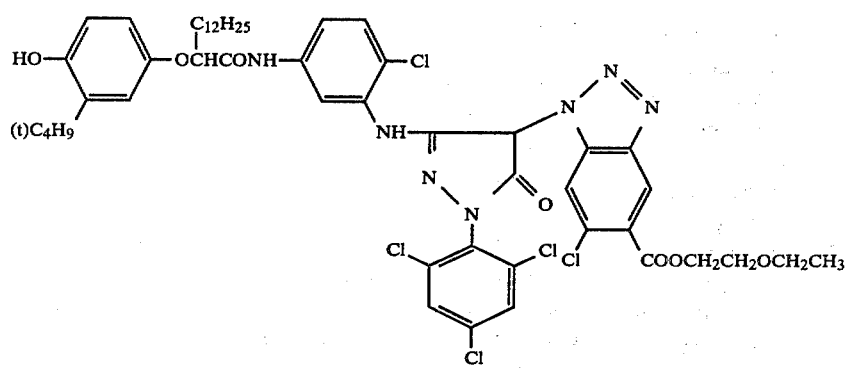
(3)
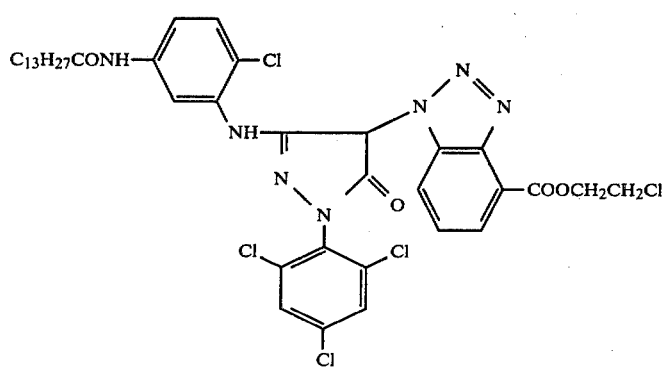
(4)

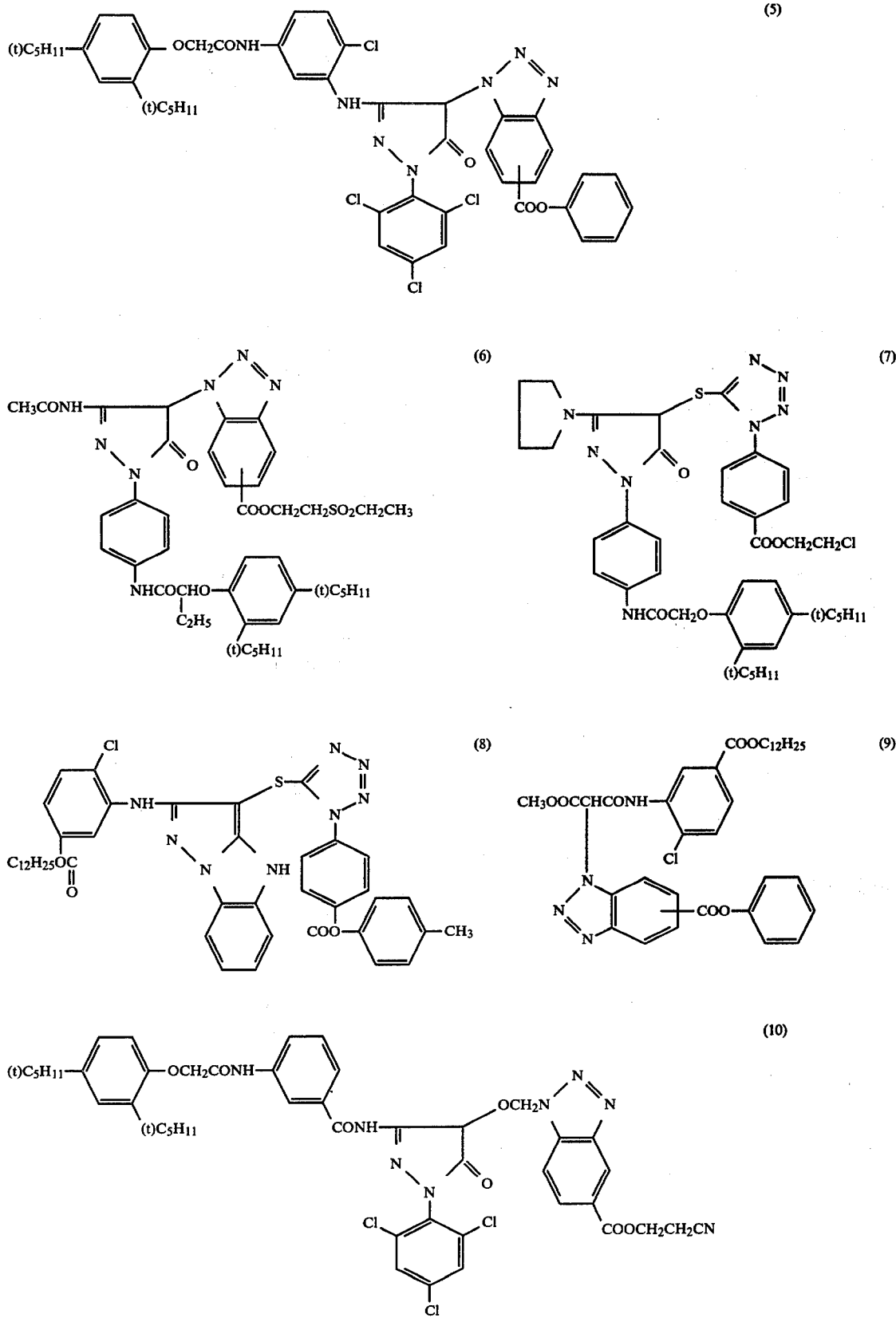

-continued
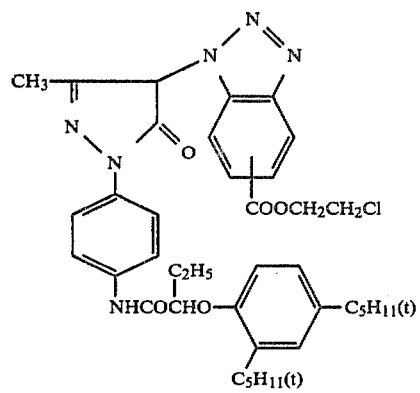 (11)
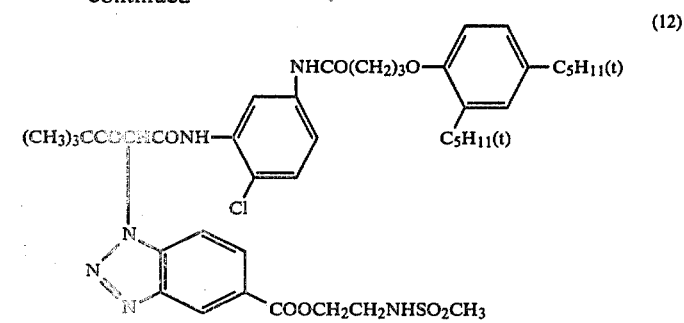 (12)
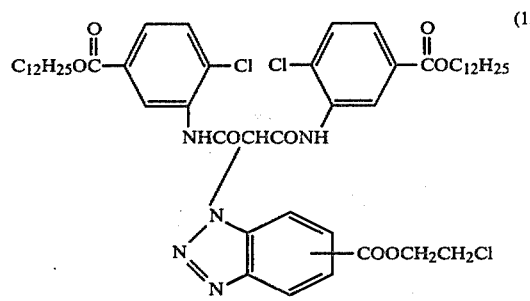 (13)
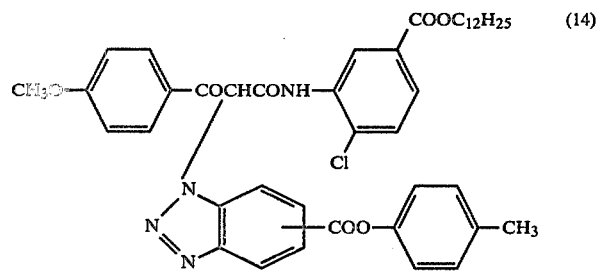 (14)
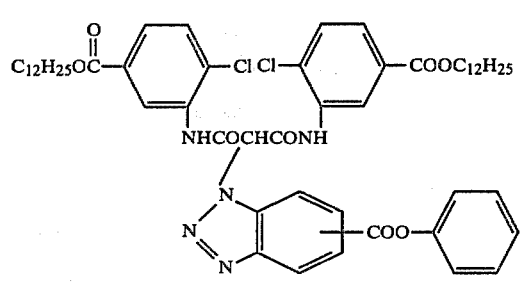 (15)
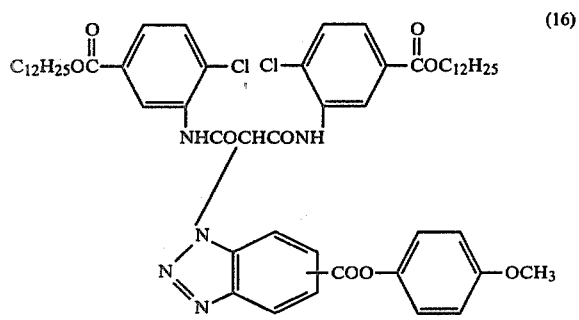 (16)
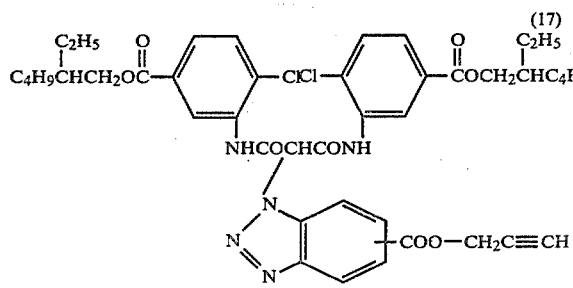 (17)
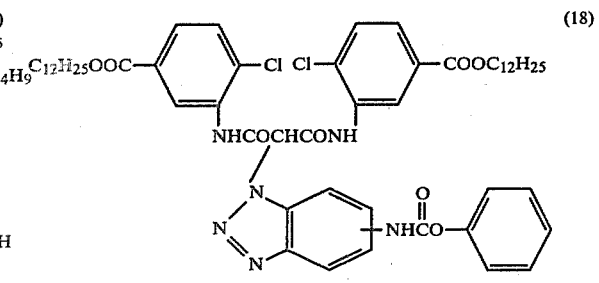 (18)
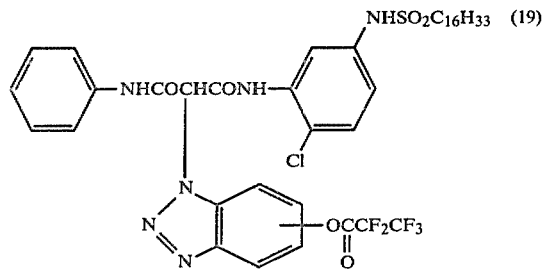 (19)
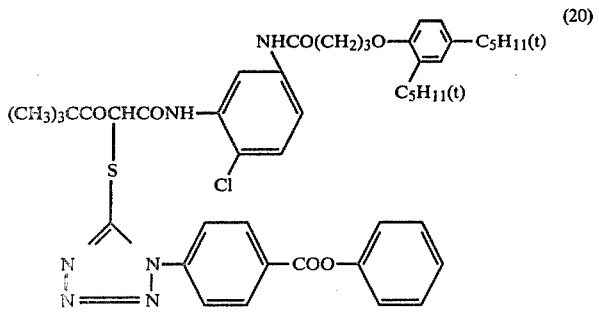 (20)

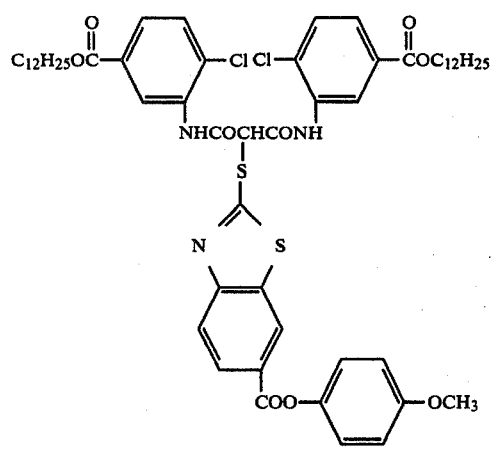
(21)
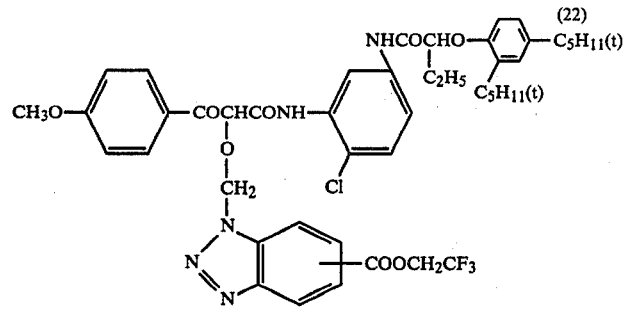
(22)
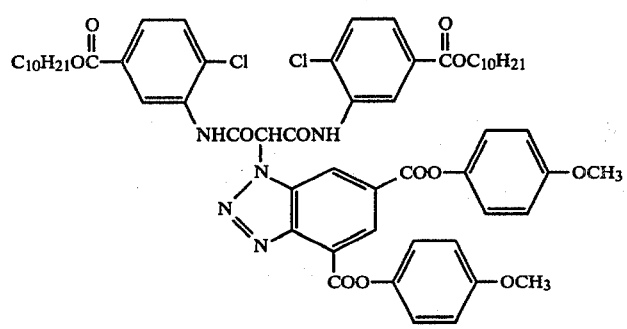
(23)
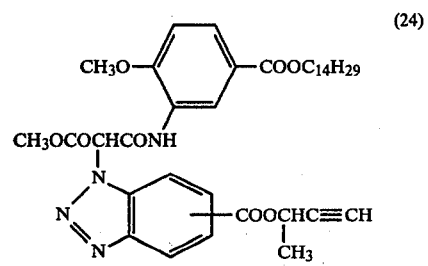
(24)
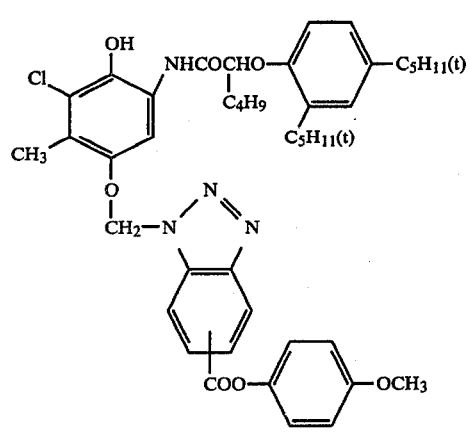
(25)
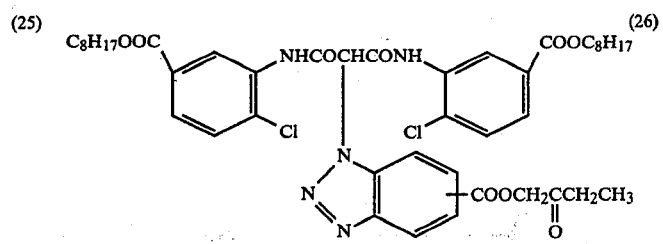
(26)
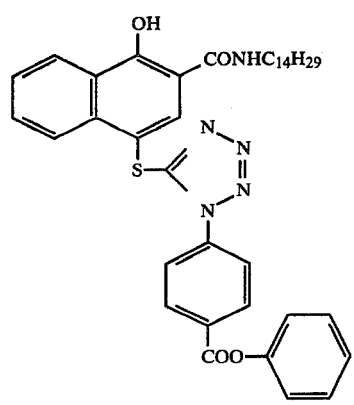
(27)
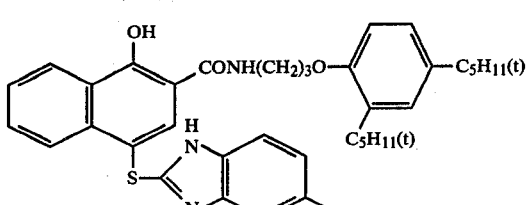
(28)

-continued
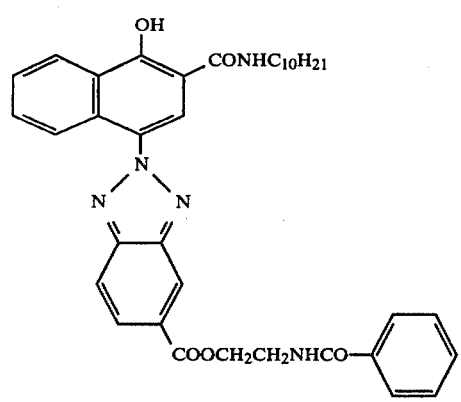
(29)
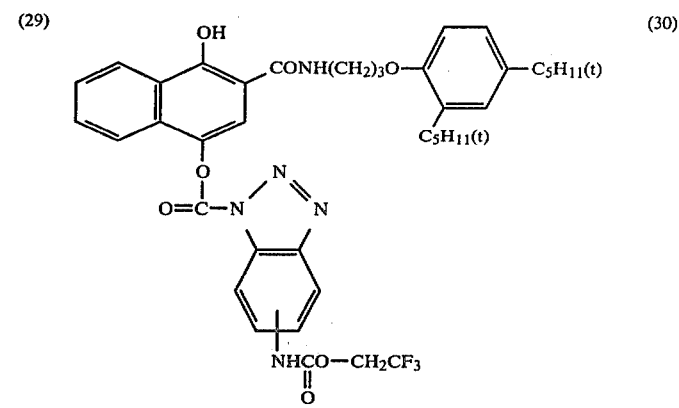
(30)
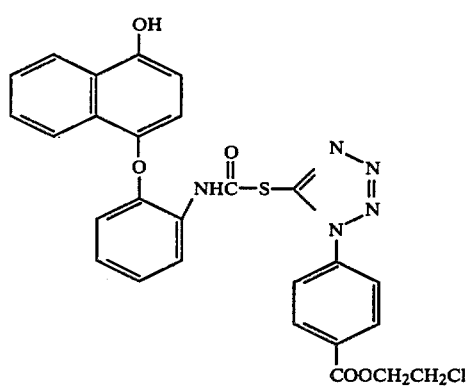
(31)
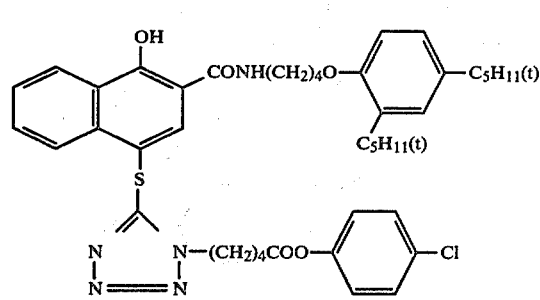
(32)
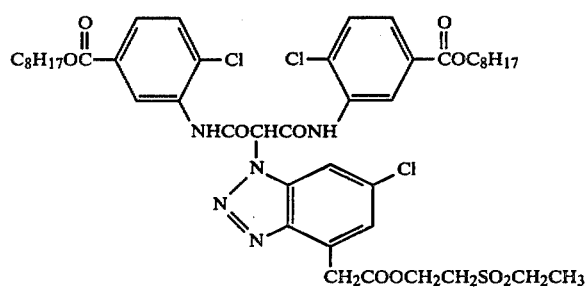
(33)
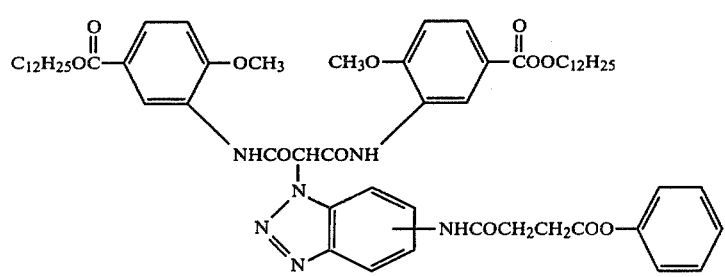
(34)

-continued
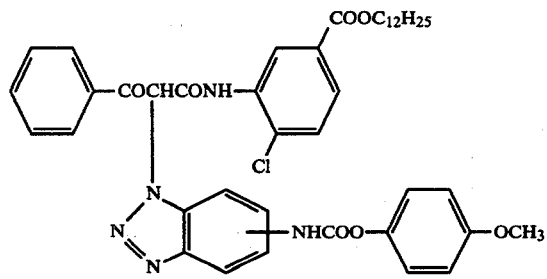 (35)
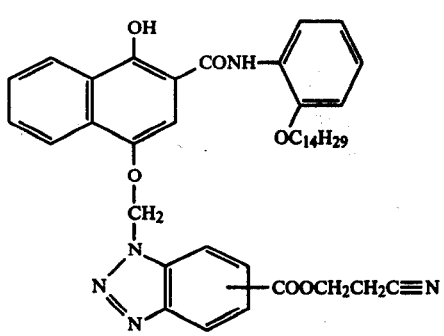 (36)
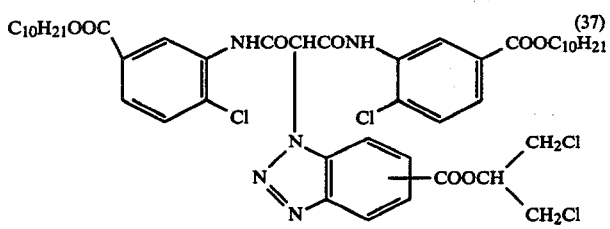 (37)
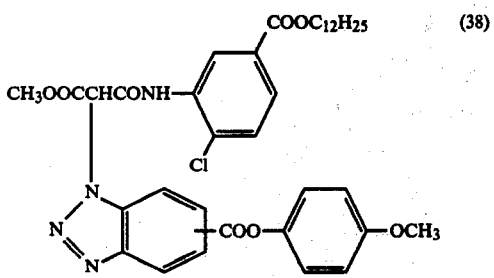 (38)
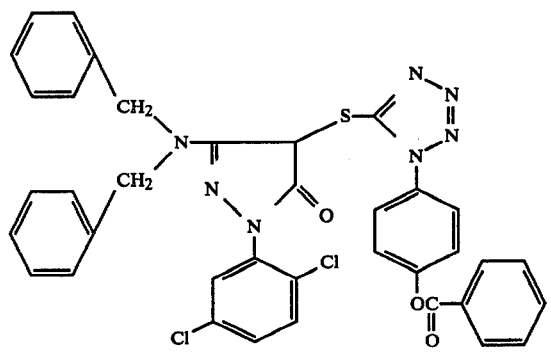 (39)
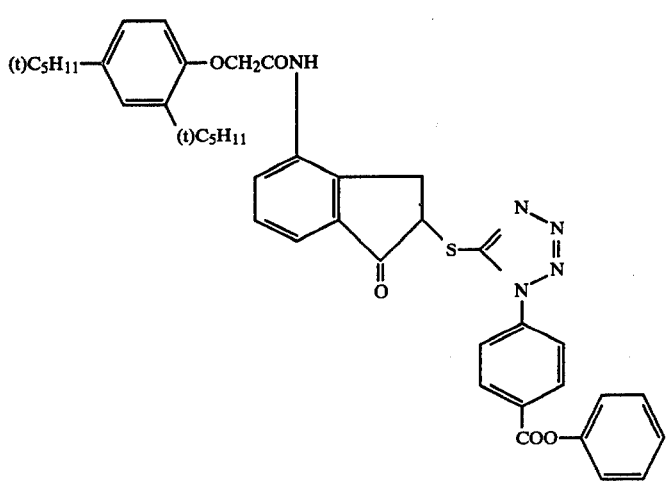 (40)

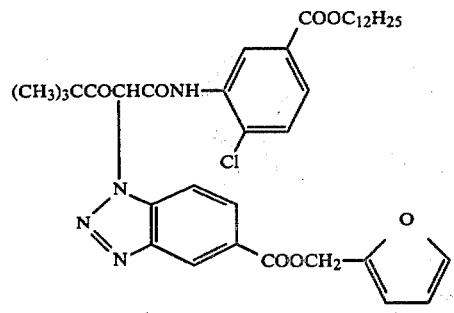 (41)
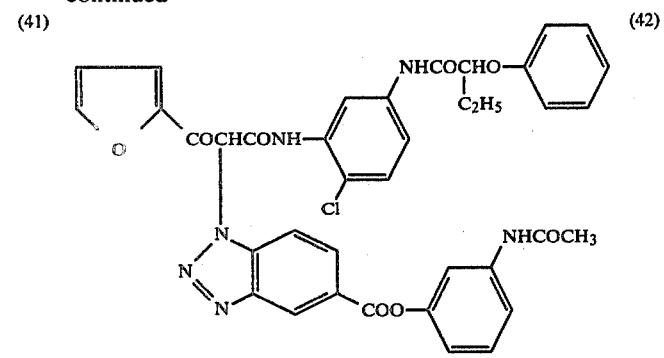 (42)
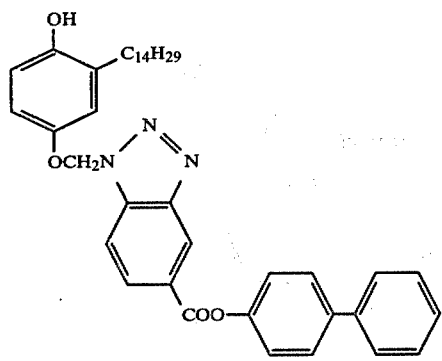 (43)
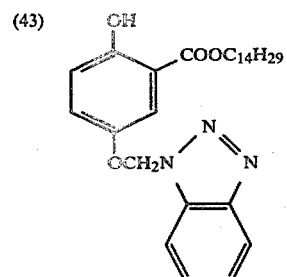 (44)
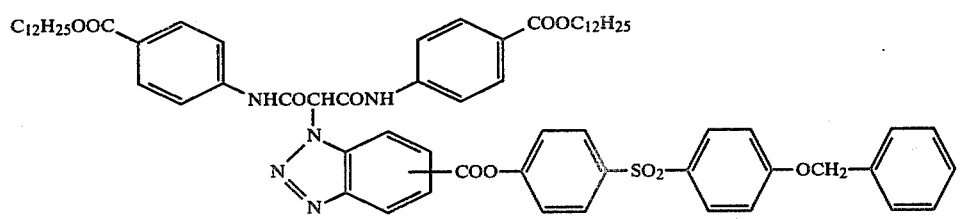 (45)
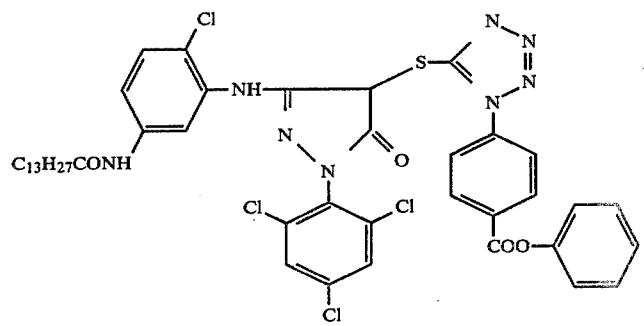 (46)
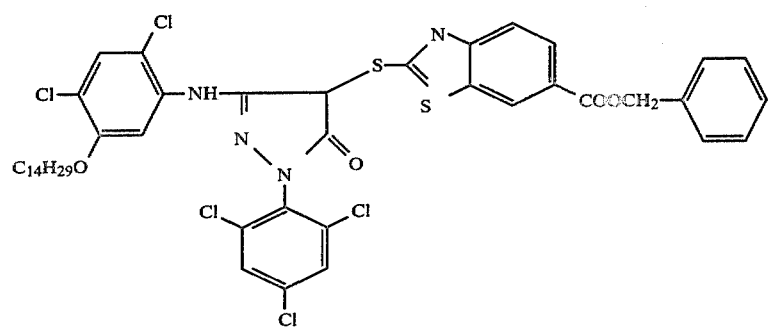 (47)

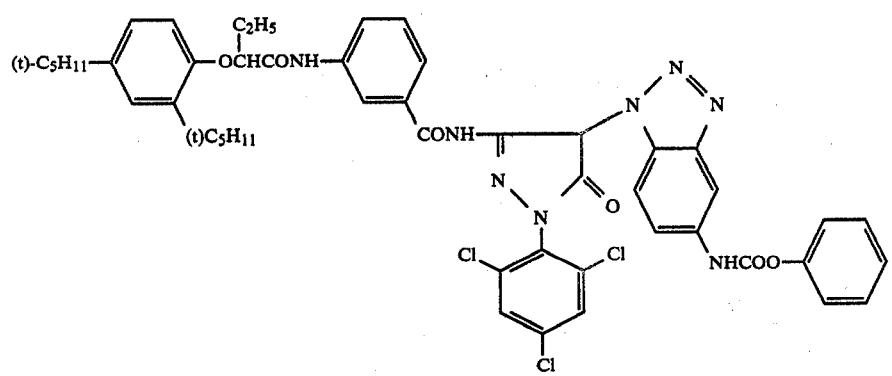
(48)
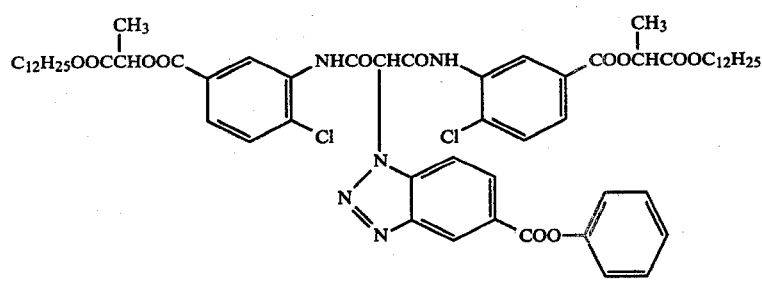
(49)
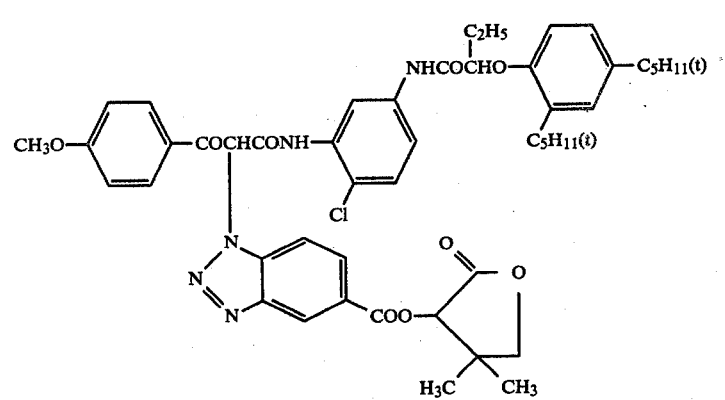
(50)
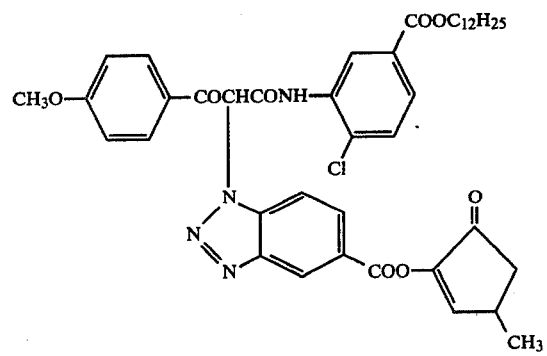
(51)
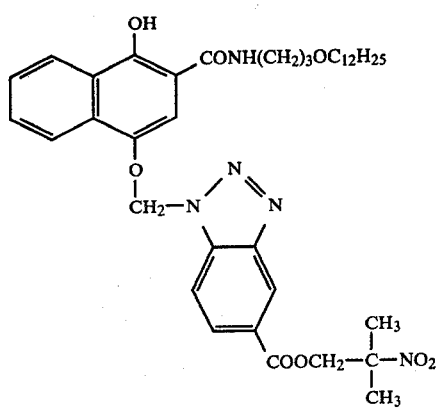
(52)

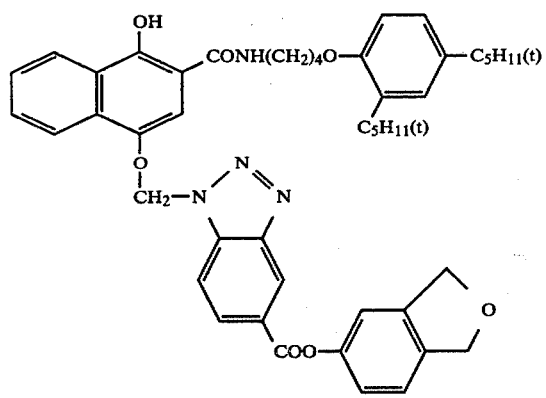
(53)
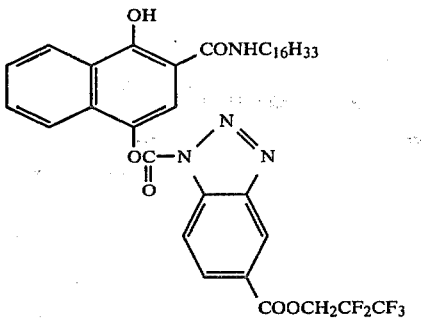
(54)
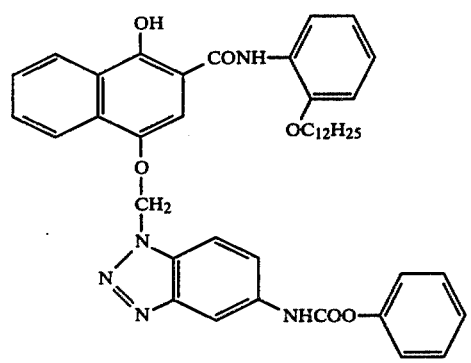
(55)
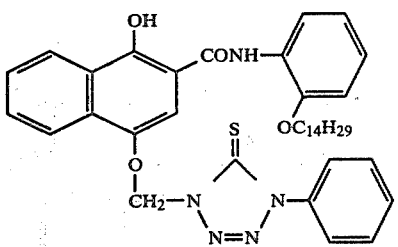
(56)
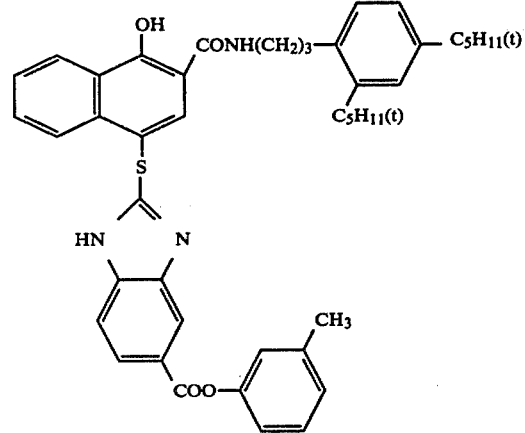
(57)
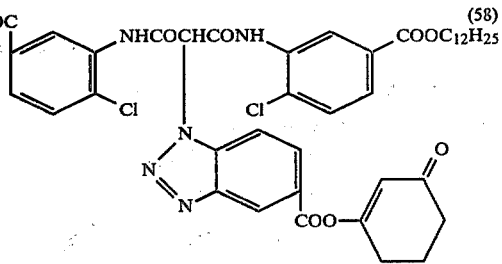
(58)
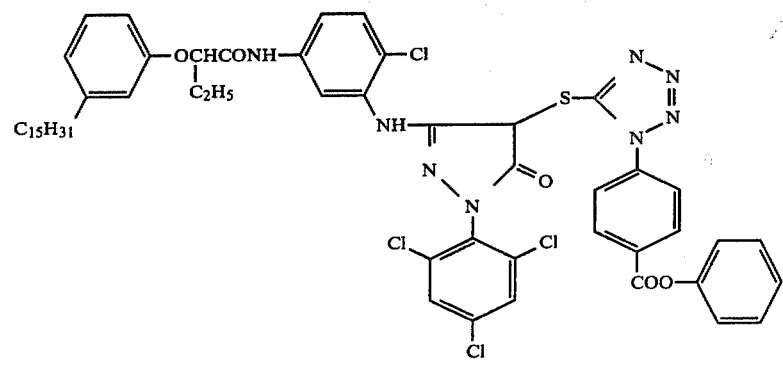
(59)

-continued
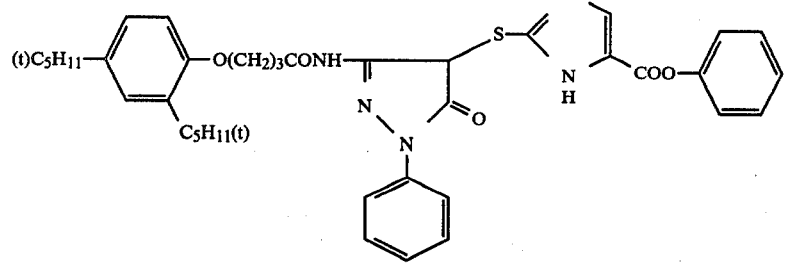
(60)
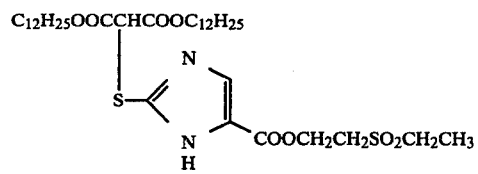
(61)
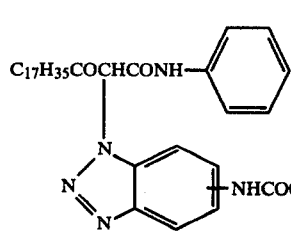
(62)
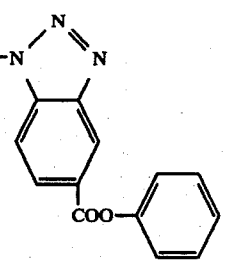
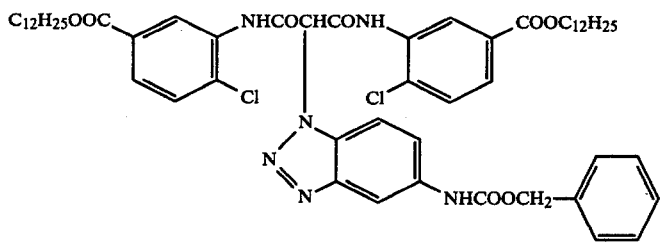
(63)
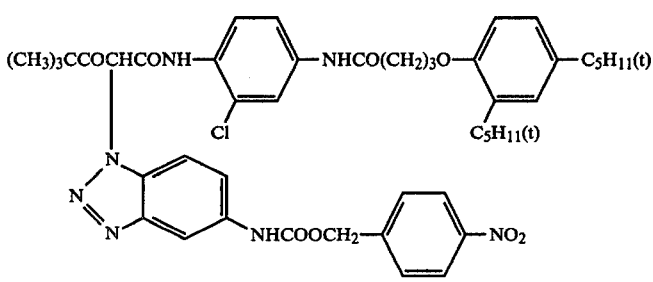
(64)
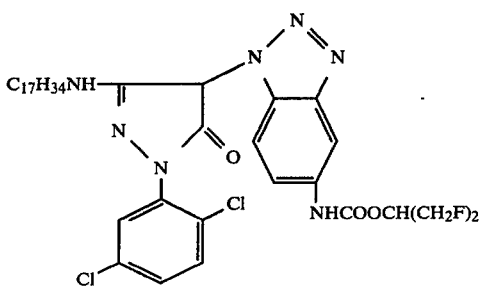
(65)
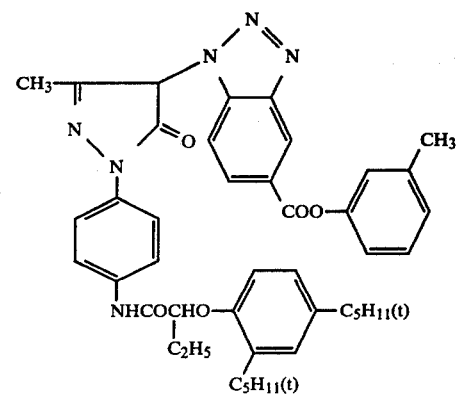
(66)

-continued
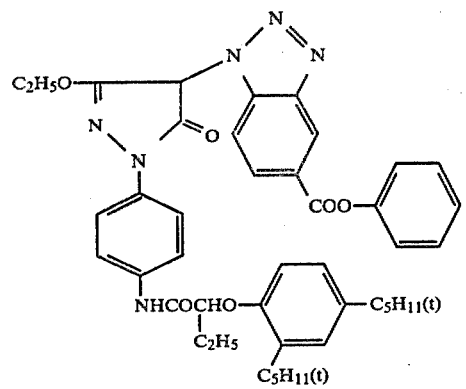 (67)
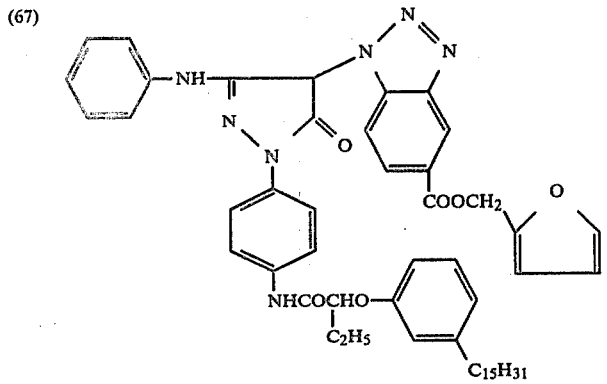 (68)
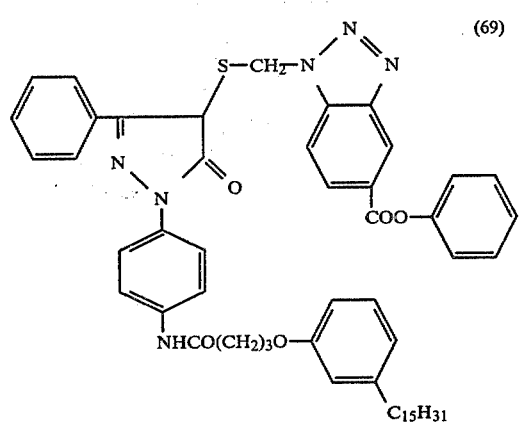 (69)
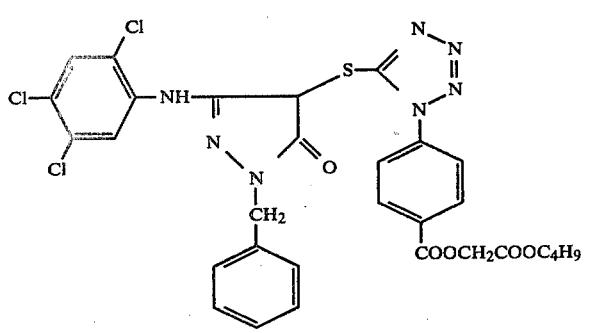 (70)
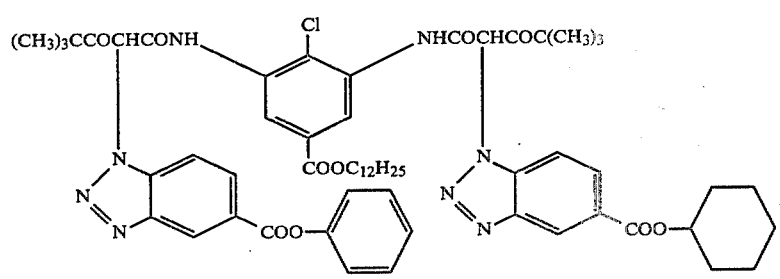 (71)
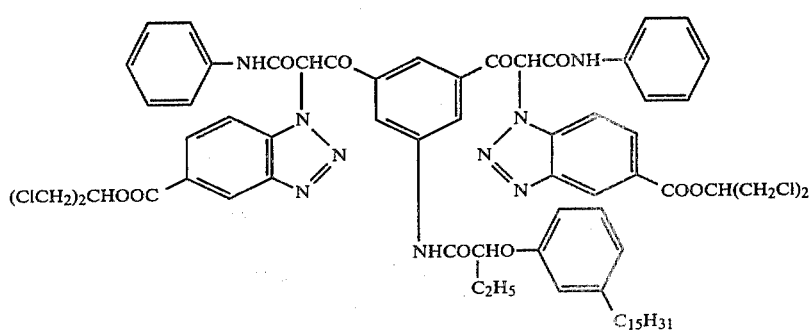 (72)

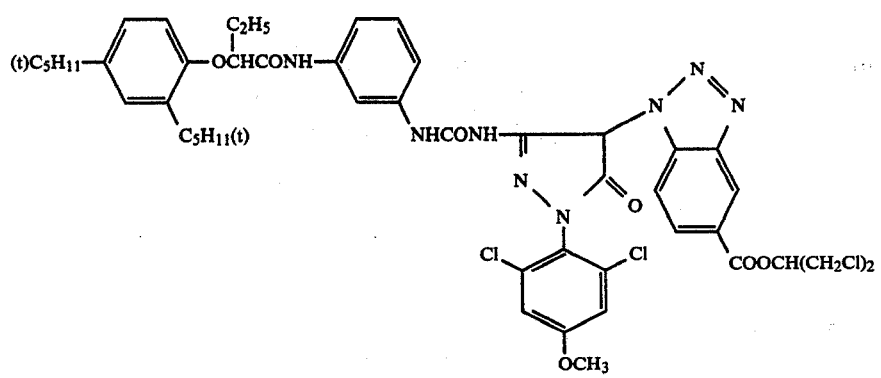
(73)
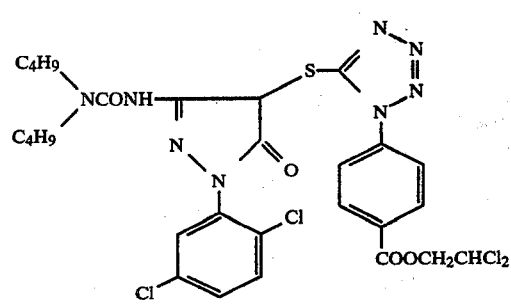
(74)
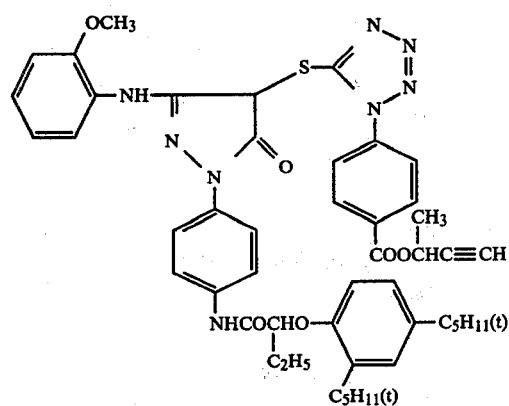
(75)
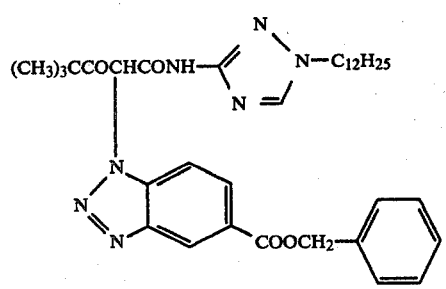
(76)
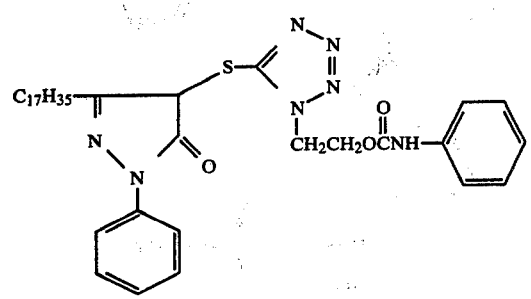
(77)
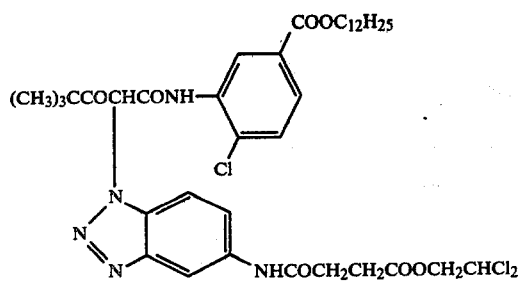
(78)
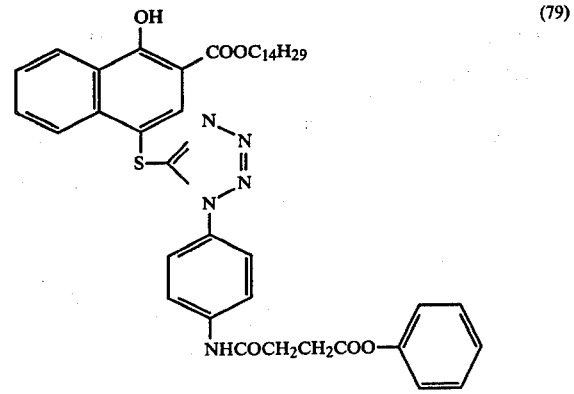
(79)

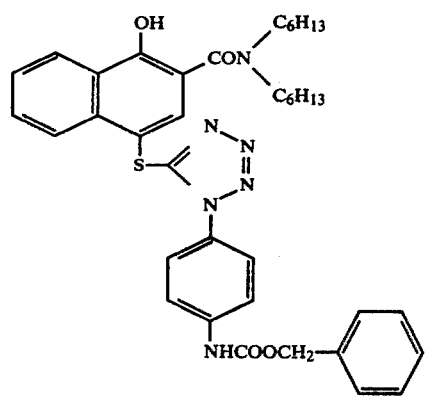
(80)
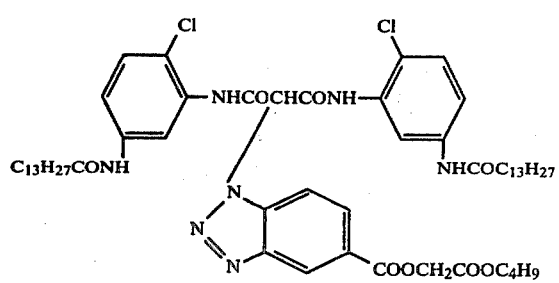
(81)
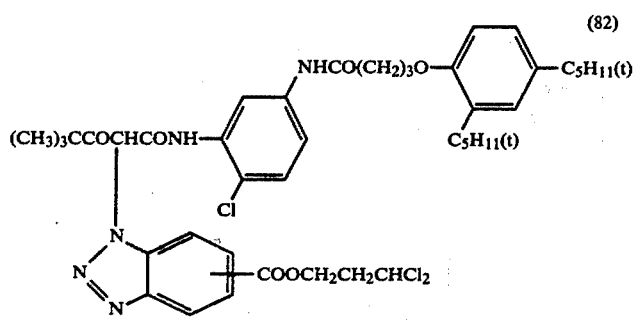
(82)
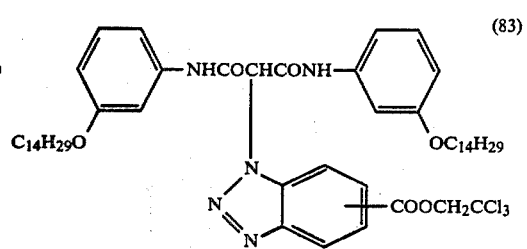
(83)
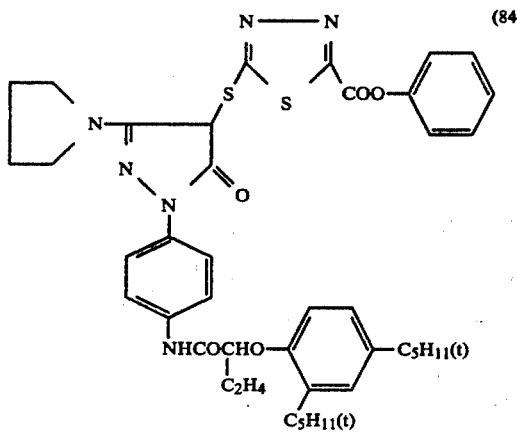
(84)
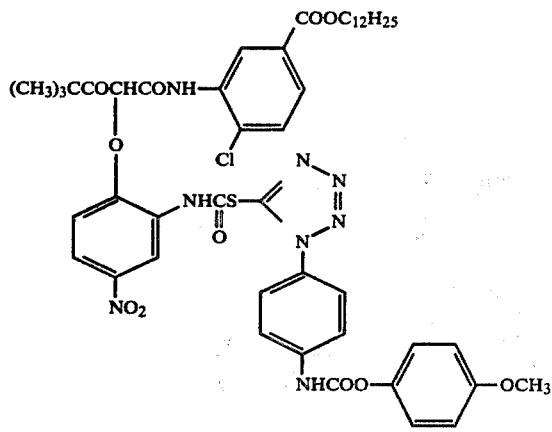
(85)
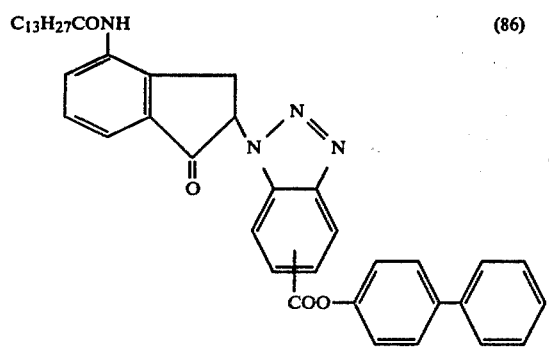
(86)
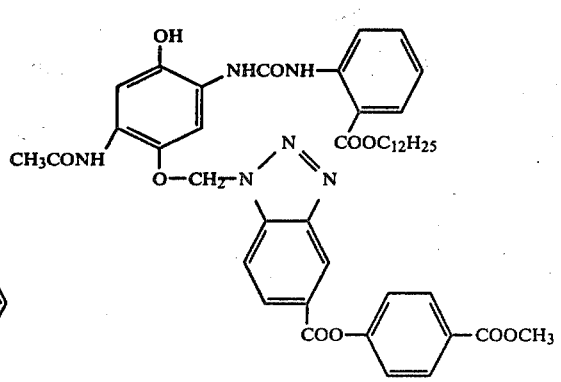
(87)

-continued
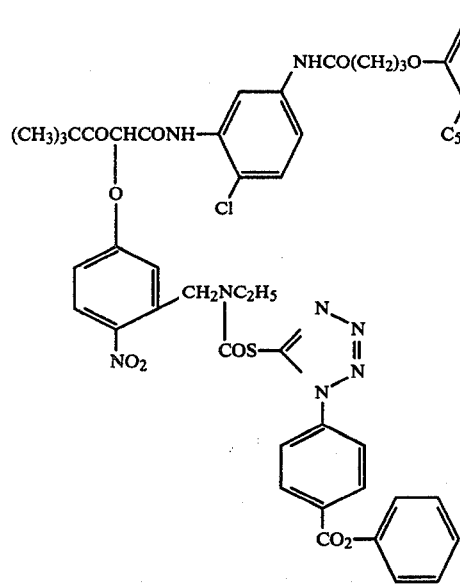
(88)
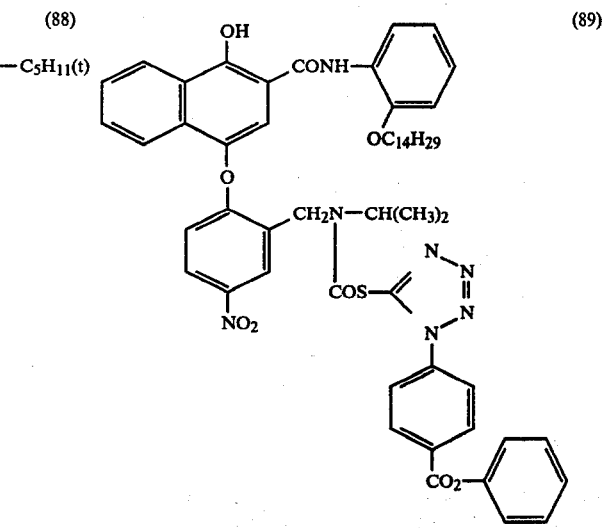
(89)
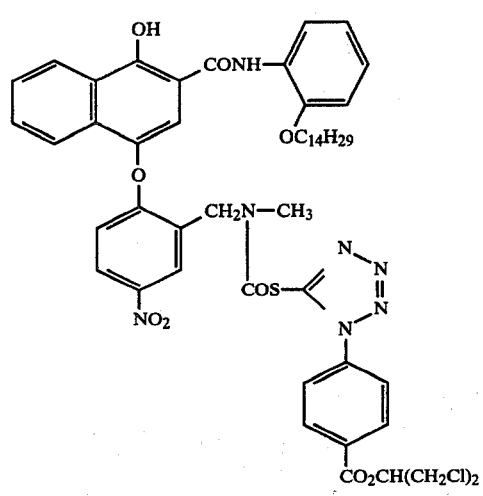
(90)
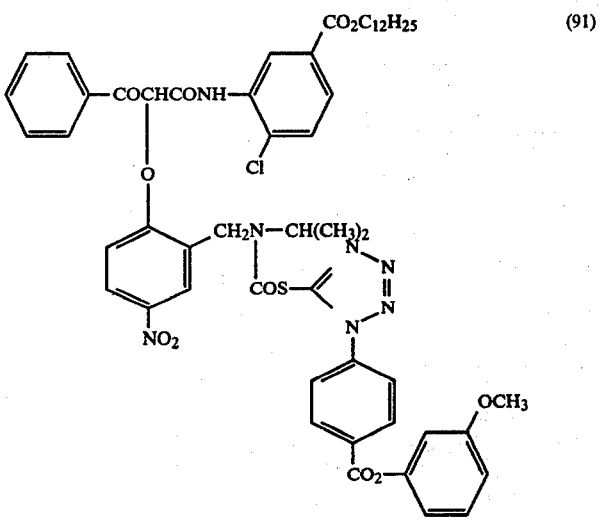
(91)
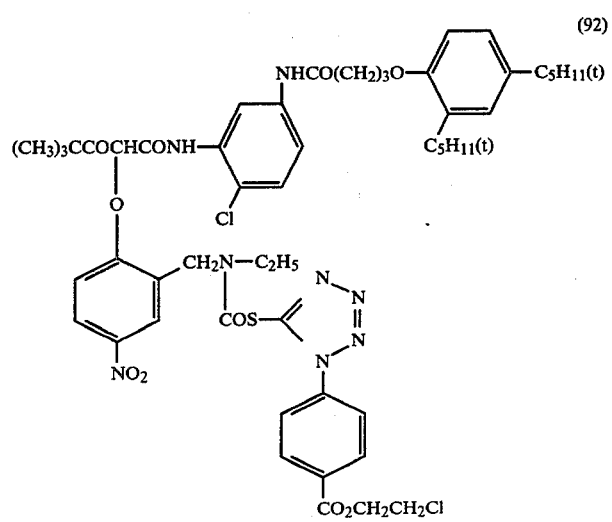
(92)
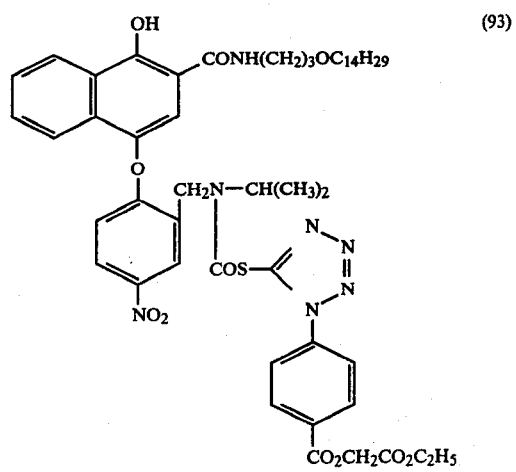
(93)

-continued

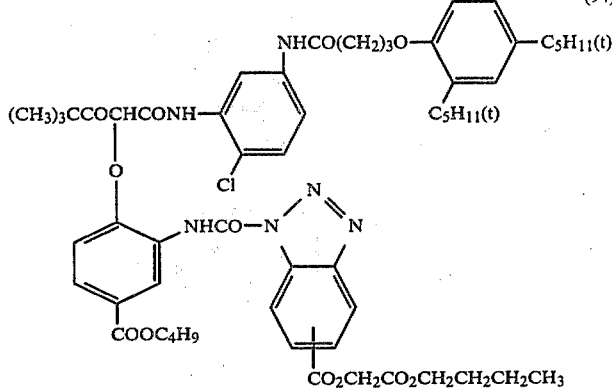
(94)

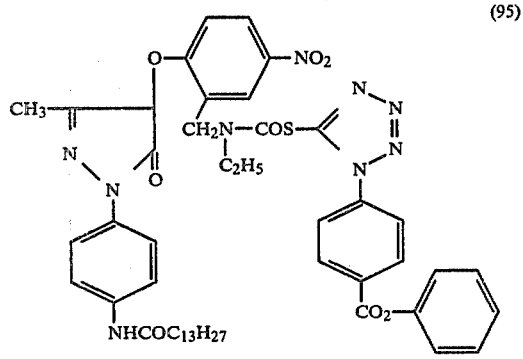
(95)

Most couplers according to the present invention can be easily synthesized, in general, using a reaction as shown below.

(A) Synthesis of a coupler represented by formula (II)
The coupler can be synthesized according to the method as described in, for example, U.S. Pat. No. 3,227,554, etc. The reaction scheme is shown below.

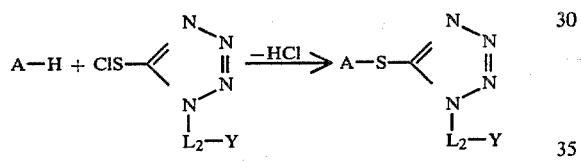

wherein A, $L_2$ and Y each has the same meaning as defined in formula (II) above. In the above, sulfenyl chloride can be synthesized by a commercially known reaction of thiol with sulfuryl chloride.

(B) Synthesis of a coupler represented by formula (III)
The coupler can be synthesized according to the method as described in, for example, U.S. Pat. Nos. 4,076,533 and 3,933,500, etc. The reaction scheme is shown below.

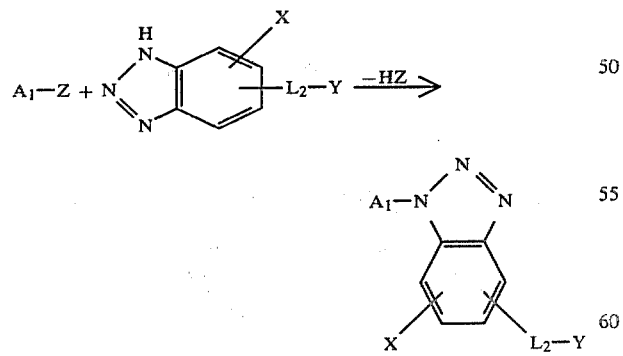

wherein $A_1$, X, $L_2$ and Y each has the same meaning as defined above, and Z represents a halogen atom (for example, a chlorine atom, a bromine atom, etc.) which is bonded at the coupling position of the coupler.

(C) Synthesis of a coupler represented by formula (IV)

The coupler can be synthesized according to the method as described in, for example, U.S. Pat. No. 4,146,396, etc. The reaction scheme is shown below.

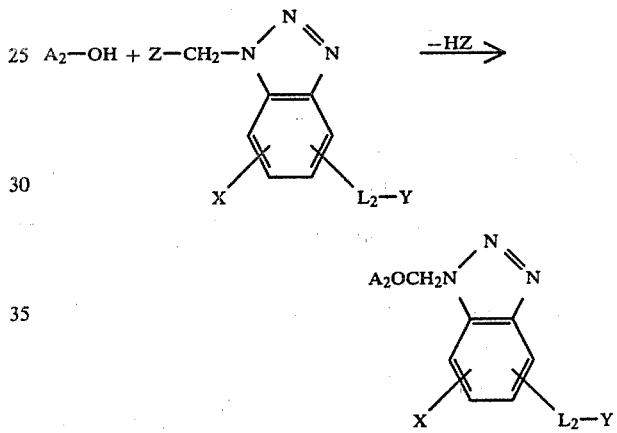

wherein $A_2$, X, $L_2$ and Y each has the same meaning as defined above, and Z represents a halogen atom (for example, a chlorine atom, a bromine atom, etc.). A method for introducing a hydroxy group into the coupling position (synthesis of a compound represented by the formula $A_2OH$) is described in U.S. Pat. No. 3,311,476.

Typical synthesis examples of the couplers according to the present invention are specifically set forth below.

SYNTHESIS EXAMPLE 1

Synthesis of Coupler (14)

The coupler can be synthesized through a synthesis route described below.

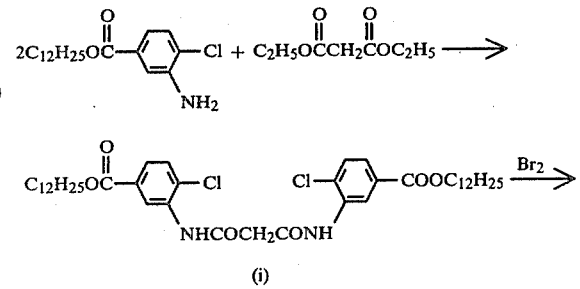
(i)

-continued

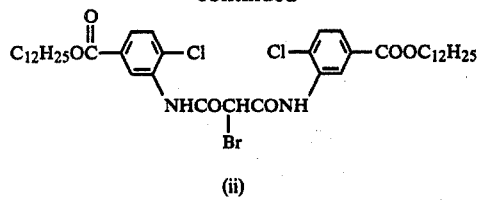

(ii)

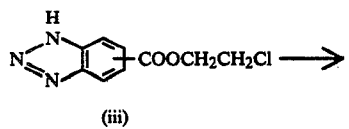

(iii)

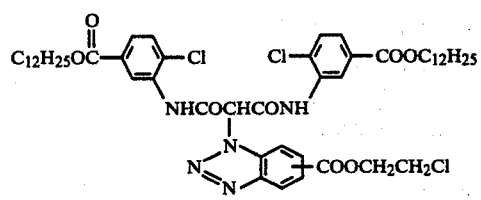

Step 1: Synthesis of Compound (i)

170 g of 2-chloro-5-dodecyloxycarbonylaniline and 40 g of diethyl ester of malonic acid were stirred at 200° C. for 15 hours. The reaction mixture was poured into 1,500 ml of ethanol and the solid thus deposited was collected by filtration to obtain 150 g of the desired compound. A melting point was 94° to 96° C.

Step 2: Synthesis of Compound (ii)

50 g of Compound (i) obtained in Step 1 was dissolved in 500 ml of acetic acid and 12 g of bromine was added dropwise to the solution. After stirring at room temperature for 1 hour, the reaction mixture was poured into 1 liter of water. The solid thus deposited was collected by filtration to obtain 55 g of the desired compound which was used in Step 4 without further purification.

Step 3: Synthesis of Compound (iii)

100 g of 5- (or 6-)carboxybenzotriazole was suspended in 500 ml of 2-chloroethanol and heated at 60° C. to 80° C. with stirring. A hydrogen chloride gas was introduced through the solution for 4 hours. The solvent was distilled off under reduced pressure until the volume of the reaction mixture became almost half. The residue was poured into 1 liter of water containing 5% of sodium hydrogencarbonate and the solid thus deposited was collected by filtration.

Step 4: Synthesis of Coupler (14)

22 g of Compound (iii) obtained in Step 3 and 10 g of triethylamine were dissolved in 150 ml of chloroform. To the solutiion was added dropwise at room temperature a solution containing 40 g of Compound (iii) obtained in Step 3 dissolved in 200 ml of chloroform. After stirring for 1 hour at room temperature, the reaction mixture was washed with water. Then the mixture was washed with diluted hydrochloric acid and washed several times with water until the liquid became neutral. The oily layer was separated and the floating crystals were removed by filtration. The filtrate was concentrated under reduced pressure and the residue was crystallized with acetonitrile to obtain 35 g of the desired coupler. A melting point was 81° to 91° C.

SYNTHESIS EXAMPLE 2

Synthesis of Coupler (16)

The coupler can be synthesized through a synthesis route described below.

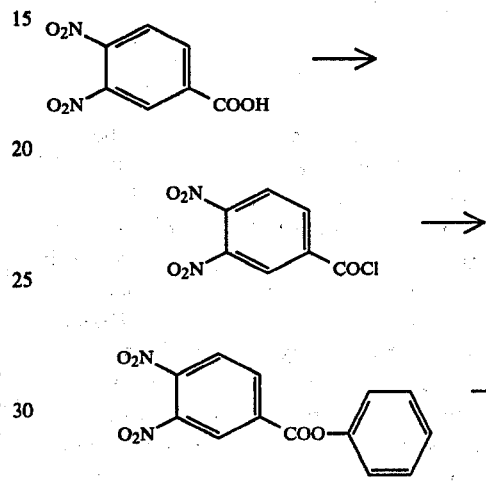

(i)

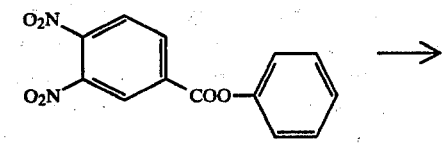

(ii)

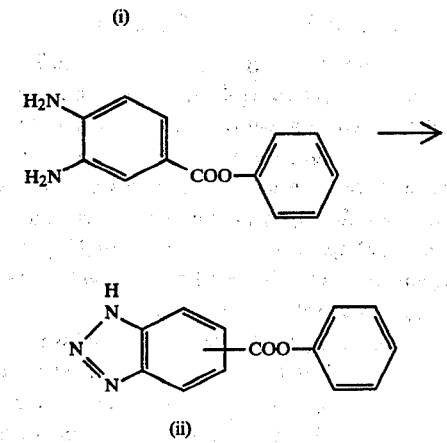

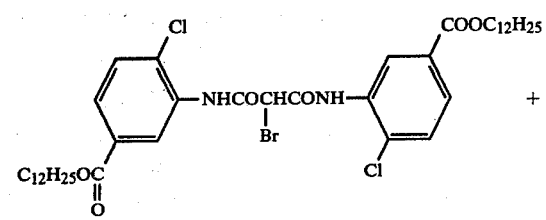

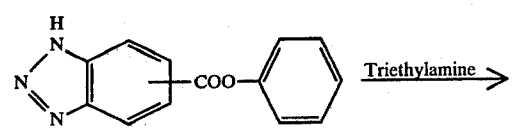

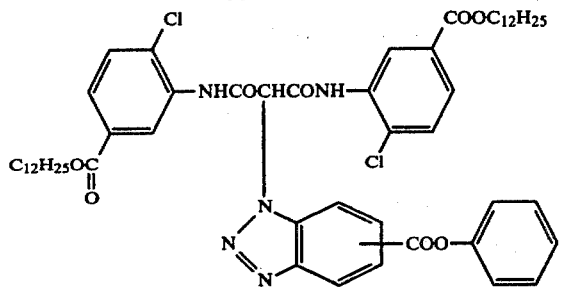

Coupler (16)

Step 1: Synthesis of Compound (i)

A mixture of 50 g (0.24 mol) of 3,4-dinitrobenzoic acid, 34 g (0.29 mol) of thionyl chloride and 300 ml of toluene was refluxed by heating with stirring for 3 hours. The excess amount of thionyl chloride and toluene were distilled off under reduced pressure to obtain raw 3,4-dinitrobenzoic acid chloride. To the acid chloride were added 34 g (0.36 mol) of phenol and 100 ml of toluene, and a mixture was refluxed by heating with stirring for 5 hours. After cooling to room temperature, the crystals thus formed were collected by filtration to obtain 55 g (yield 80%) of phenyl ester of 3,4-dinitrobenzoic acid.

Step 2: Synthesis of Compound (ii)

300 ml of acetic acid was added to 52 g (0.18 mol) of phenyl ester of 3,4-dinitrobenzoic acid and 150 g (2.7 mol) of reduced iron and the mixture was heated at 90° C. with stirring to which 20 ml of water was added dropwise over a period of 30 minutes. The reaction solution was filtered and the filtrate was allowed to stand for cooling. A solution containing 22 g (0.26 mol) of sodium nitrite dissolved in 100 ml of water was added dropwise to the solution while maintaining a reaction temperature below 5° C. over a period of 1 hour. After adding 100 ml of water, the precipitate thus formed was filtered to obtain raw crystals of 5-phenoxycarbonylbenzotriazole. The raw crystals were recrystallized from benzene to obtain 32 g (yield 75%) of 5-phenoxycarbonylbenzotriazole. The melting point was 156° to 160° C.

Step 3: Synthesis of Coupler (16)

24 g (0.1 mol) of 5-phenoxycarbonylbenzotriazole and 10 g (0.1 mol) of triethylamine were dissolved in 200 ml of chloroform and to the solution was added dropwise 41 g (0.5 mol) of 2-bromomalonic acid bis(2-chloro-5-dodecyloxycarbonylanilide) dissolved in 300 ml of chloroform at room temperature with stirring over a period of 1 hour. After stirring for 1 hour, the reaction solution was filtered and the filtrate was washed with diluted hydrochloric acid and then with water. The filtrate was dried with sodium sulfate and concentrated to obtain the desired compound as the oily product. Upon recrystallization from methanol 41 g (yield 84%) of the desired compound was obtained. The melting point was 84° to 94° C.

| | Elemental Analysis: | | |
|---|---|---|---|
| | H | C | N |
| Calcd. (%) | 6.86 | 65.84 | 7.11 |
| Found (%) | 6.95 | 66.01 | 7.06 |

SYNTHESIS EXAMPLE 3

Synthesis of Coupler (27)

1-Hydroxymethyl-5(6)-propyloxycarbonylbenzotriazole prepared from 5(6)-propyloxycarbonylbenzotriazole and formaldehyde was reacted with 3 times the molar quantity of thionyl chloride to synthesize 1-chloromethyl-5(6)-propyloxycarbonylbenzotriazole. The latter was reacted with equimolar amount of 1,4-dihydroxy-N-[γ-(2,4-di-tert-amylphenoxy)propyl]-2-naphthamide in dimethylformamide in the presence of 2 times the molar quantity of sodium ethoxide to obtain Coupler (27).

SYNTHESIS EXAMPLE 4

Synthesis of Coupler (29)

2-(4-Phenoxycarbonylphenyl)tetrazolylsulfenyl chloride prepared from 2-(4-phenoxycarbonylphenyl)tetrazolythiol and sulfuryl chloride was reacted with equimolar amount of 1-hydroxy-N-tetradecyl-2-naphthamide in chloroform under reflux to obtain Coupler (29).

SYNTHESIS EXAMPLE 5

Synthesis of Coupler (37)

5(6)-(4-Methoxyphenoxycarbonylamino)benzotriazole prepared from 5(6)-aminobenzotriazole and 4-methoxyphenoxycarbonyl chloride was reacted with 2-benzoyl-2-bromo-2'-chloro-5'-dodecyloxycarbonylacetanilide in dimethylformamide in the presence of triethylamine to obtain Coupler (37).

SYNTHESIS EXAMPLE 6

Synthesis of Coupler (40)

5(6)-Carboxybenzotriazole and 4-methoxyphenol were subjected to dehydration condensation using dicyclohexylcarbodiimide to obtain 5(6)-(4-methoxyphenoxycarbonyl)benzotriazole. The latter was reacted with α-bromo-2'-chloro-5'-dodecyloxycarbonyl malonmonoanilide methyl ester in dimethylformamide in the presence of triethylamine to obtain Coupler (40).

SYNTHESIS EXAMPLE 7

Synthesis of Coupler (90)

The coupler can be synthesized through a synthesis route described below.

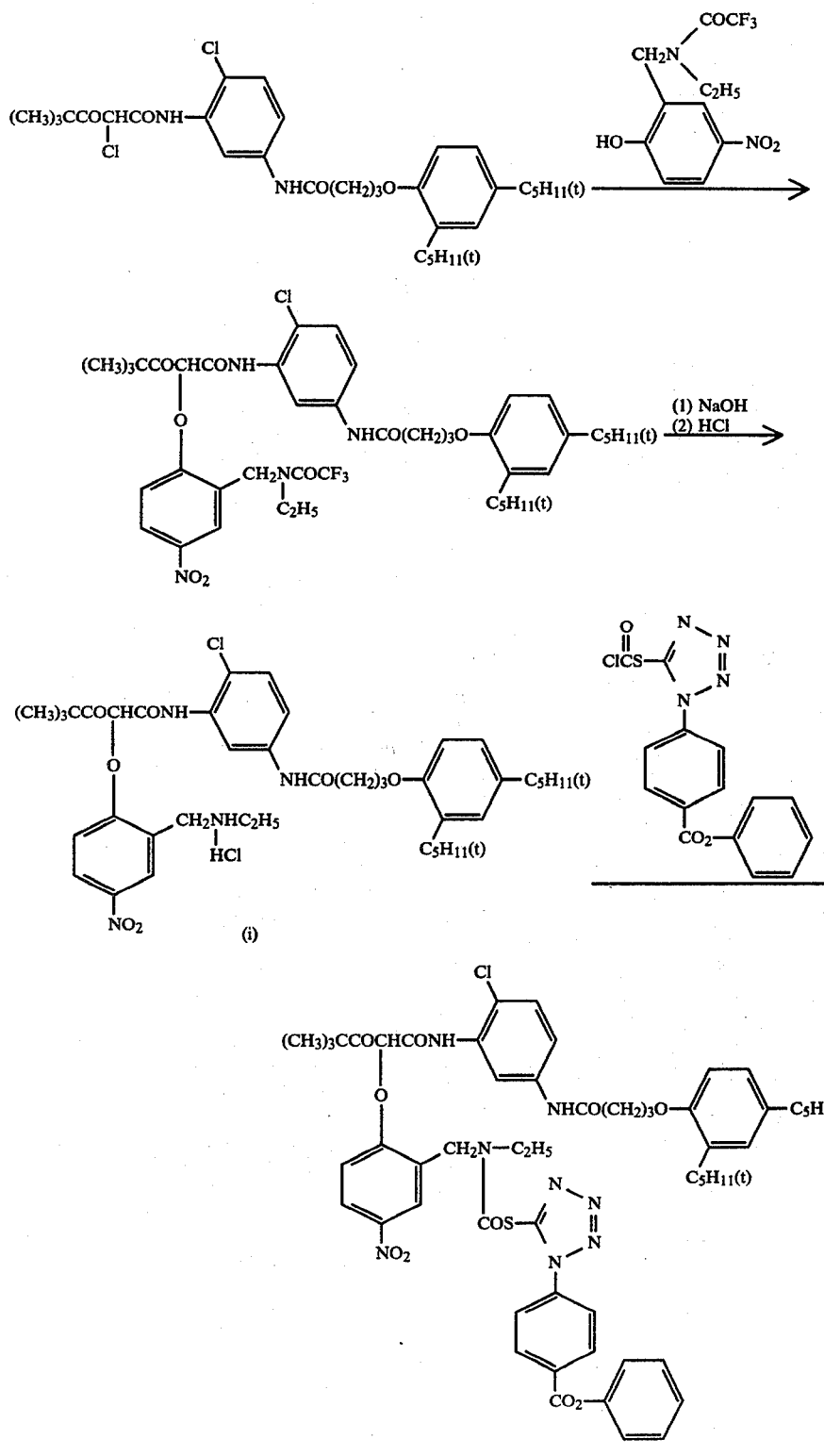
(90)
Step 1: Synthesis of Compound (i)
To a solution of 32 g of 2-(N-ethyltrifluoroacetamido)methyl-4-nitrophenol in 500 ml of acetonitrile were added 11.5 g of triethylamine and 62.9 g of 2-pivalyl-2-chloro-[2-chloro-5-{4-(2,4-di-tert-amyl)-phenoxy}butyramido]acetanilide with stirring. The resulting solution was refluxed for 2.5 hours and then concentrated under reduced pressure. The residue was dissolved in 400 ml of methanol. To the resulting solution was added dropwise a solution of 40 g of sodium hydroxide in 100 ml of water. During the addition, the reaction temperature was kept at 20° C. or less by water cooling. After stirring for 1 hour, the reaction mixture was poured into 2,000 ml of ice water containing 400 ml of concentrated hydrochloric acid. Crystals which formed were collected by filtration and recrystallized from ethyl acetate to give 65.6 g of Compound (i).

Step 2: Synthesis of Coupler (90)

28.3 g of Compound (i) obtained in Step 1 above was suspended in 400 ml of ethyl acetate. To this suspension was added 225 ml of saturated aqueous sodium hydrogencarbonate solution with stirring at room temperature. After stirring for 20 minutes was separated the oily layer to which 26 g of 2-(4-phenoxycarbonylphenyl)tetrazolylthiocarbonyl chloride and 7 g of triethylamine were added. After stirring for 1 hour, crystals which formed were removed by filtration and the filtrate was concentrated. The concentrated filtrate was subjected to silica gel column chromatography using a column charged with 500 g of silica gel and a mixed solvent consisting of hexane and ethyl acetate (2:1) as an eluant to concentrate the fraction containing the objective compound, thus yielding 8.9 g of Coupler (90).

The couplers according to the present invention are roughly classified into two groups: one being Fischer type couplers having a water-soluble group, for example, a carboxy group, a hydroxy group, a sulfo group, etc.; and the other being hydrophobic couplers.

As a method for the addition of the couplers to an emulsion or as a method for the dispersion of the couplers in an emulsion or as a method for the addition thereof to a gelatino-silver halide emulsion or hydrophilic colloid, those conventionally known in the art can be applied. For example, a method in which the coupler is mixed with a high boiling organic solvent such as dibutyl phthalate, tricresyl phosphate, wax, higher fatty acid or the ester thereof to disperse (as described in, e.g., U.S. Pat. Nos. 2,304,939, 2,322,027, etc.), a method in which the coupler is mixed with a low-boiling organic solvent or a water-soluble organic solvent to disperse, a method of dispersing the coupler using a high-boiling solvent in combination with them (as described in, e.g., U.S. Pat. Nos. 2,801,170, 2,801,171, 2,949,360, etc.), and, when the coupler itself has a sufficiently low melting point (for example, not more than 75° C.), a method of dispersing the coupler alone or in combination with other couplers to be used together, such as a colored coupler or an uncolored coupler (as described in, e.g., German Pat. No. 1,143,707, etc.), can be used. In the above methods suitable examples of low boiling solvents are methyl acetate, ethyl acetate, butyl acetate, sec-butyl alcohol and of water-miscible solvents are tetrahydrofuran, cyclohexanone, methyl cellosolve, ethylene glycol, acetone, ethanol, etc.

As the dispersing aid, conventionally used anionic surface active agents (e.g., sodium alkylbenzenesulfonates, sodium dioctylsulfosuccinate, sodium dodecylsulfate, sodium alkylnaphthalenesulfonates, Fischer type couplers, etc.), amphoteric surface active agents (e.g., N-tetradecyl-N,N-dipolyethylene-$\alpha$-betaine, etc.), and nonionic surface active agents (e.g., sorbitan monolaurate, etc.) can be used.

The emulsion which is used in the present invention is a gelatino-silver halide photographic emulsion containing grains of silver chloride, silver bromide, silver iodide, or mixed silver halides.

Hydrophilic colloids which can be used include gelatin, cellulose derivatives, alginates, hydrophilic synthetic polymers (e.g., polyvinyl alcohol, polyvinyl pyrrolidone, polystyrene sulfonic acid, etc.), and the like. Furthermore, a plasticizer for improving the dimensional stability of films and polymer latex such as polymethyl methacrylate, polyethyl acrylate, etc., can be used.

To the silver halide emulsion used in the present invention can be applied a conventionally employed chemical sensitizing methods, for example, gold sensitization as described in U.S. Pat. Nos. 2,399,083, 2,597,856, and 2,597,915; reduction sensitization as described in U.S. Pat. Nos. 2,487,850 and 2,521,925; sulfur sensitization as described in U.S. Pat. Nos. 1,623,499 and 2,410,689; a sensitizing method using different metal ions as described in U.S. Pat. Nos. 2,448,060, 2,566,245 and 2,566,263 or a combination thereof.

In addition, spectral sensitizing methods conventionally used for color photographic light-sensitive materials can also be employed.

Furthermore, conventional addenda such as a stabilizer (e.g., a 4-hydroxy-1,3,3a,7-tetraazaindene derivative, etc.), and an anti-fogging agent (e.g., a mercapto compound, a benzotriazole derivative, etc.), a coating aid, a hardening agent, a wetting agent, a sensitizing agent (e.g., an onium derivative such as a quaternary ammonium salt as described in U.S. Pat. Nos. 2,271,623, 2,288,266 and 2,334,864) and a polyalkylene oxide derivative as described in U.S. Pat. Nos. 2,708,162, 2,531,832, 2,533,990, 3,210,191 and 3,158,484 can be used.

Also, irradiation preventing dyes, and as a constituent for the stratum of the color photographic light-sensitive material of the present invention, such as a filter layer, a mordant-dyeing layer or a hydrophobic dye-containing colored layer can be present.

The light-sensitive emulsion used in the present invention can be applied to various supports. Suitable such supports are, e.g., cellulose acetate films, polyethylene terephthalate films, polyethylene films, polypropylene films, glass dry plates, baryta papers, resin-laminated papers, synthetic papers, and the like.

The light-sensitive materials obtained according to the present invention are development-processed using a color developing solution containing as a color developing agent conventionally employed p-phenylenediamine derivatives, p-aminophenol derivatives, or the like. Examples of the color developing agents include, e.g., p-amino-N-$\beta$-(methanesulfoamidoethyl)-m-toluidine sesquisulfate monohydrate, diethylamino-p-phenylenediamine sesquisulfate, p-amino-N,N-diethyl-m-toluidine hydrochloride, p-amino-N-ethyl-N-$\beta$-hydroxyethylaniline sesquisulfate monohydrate, etc. Developers for color negative light-sensitive materials, color negative or positive light-sensitive materials for cinema, color paper and instant color light-sensitive materials, known in the art, can be used. For example, a color development-processing step substantially as described in Japanese Patent Publication No. 35749/70, Japanese Patent Application No. 67798/69, Japanese Patent Application (OPI) No. 24323/72, Japanese Patent Publication No. 37538/76, and in H. Gordon, *The British Journal of Photography*, Nov. 15th, 1954, p. 558-; ibid., Sept. 9th, 1955, p. 440-; ibid., Jan. 6th, 1956, p. 2-; S. Horwitz, ibid., Apr. 22nd, 1960, p. 212-; E. Gehret, ibid., Mar. 4th, 1960, p. 122-; ibid., May 7th, 1965, p. 396-; J. Meech, ibid., Apr. 3rd, 1959, p. 182-; and German Patent Application (OLS) No. 2,238,051, etc. can be used.

The concentration of the coupler used in the present invention is 0.01 to 50 mols per mol of silver halide, preferably 0.1 to 5 mols per mol of silver halide.

The present invention will now be illustrated in greater detail by reference to the following examples which, however, are not intended to limit the present invention in any way. They are given to further facilitate an understanding of the manner of application of the present invention.

EXAMPLE 1

On a cellulose triacetate film support were coated layers having the compositions set forth below to prepare a multilayer color light-sensitive material.

---
First Layer: Antihalation Layer (AHL)
A gelatin layer containing black colloidal silver.
Second Layer: Intermediate Layer (ML)
A gelatin layer containing a dispersion of 2,5-di-tert-octylhydroquinone
Third Layer: First Red-SEnsitive Emulsion Layer (RL$_1$)
A silver iodobromide emulsion (iodide content: 5 mol %)

| | silver coated amount: 1.79 g/m$^2$ |
|---|---|
| Sensitizing Dye I | $6 \times 10^{-5}$ mol per mol of silver |
| Sensitizing Dye II | $1.5 \times 10^{-5}$ mol per mol of silver |
| Coupler A | 0.04 mol per mol of silver |
| Coupler C-1 | 0.0015 mol per mol of silver |
| Coupler C-2 | 0.0015 mol per mol of silver |
| Coupler (16) | 0.0006 mol per mol of silver |

Fourth Layer: Second Red-Sensitive Emulsion Layer (RL$_2$)
A silver iodobromide emulsion (iodide content: 4 mol %)

| | silver coated amount: 1.4 g/m$^2$ |
|---|---|
| Sensitizing Dye I | $3 \times 10^{-5}$ mol per mol of silver |
| Sensitizing Dye II | $1.2 \times 10^{-5}$ mol per mol of silver |
| Coupler A | 0.005 mol per mol of silver |
| Coupler C-1 | 0.0008 mol per mol of silver |
| Coupler C-2 | 0.0008 mol per mol of silver |
| Coupler C-3 | 0.015 mol per mol of silver |
| Coupler (16) | 0.00006 mol per mol of silver |

Fifth Layer: Intermediate Layer (ML)
Same as the Second Layer
Sixth Layer: First Green-Sensitive Emulsion Layer (GL$_1$)
A silver iodobromide emulsion (iodide content: 4 mol %)

| | silver coated amount: 1.5 g/m$^2$ |
|---|---|
| Sensitizing Dye III | $3 \times 10^{-5}$ mol per mol of silver |
| Sensitizing Dye IV | $1 \times 10^{-5}$ mol per mol of silver |
| Coupler B | 0.05 mol per mol of silver |
| Coupler M-1 | 0.008 mol per mol of silver |
| Coupler (16) | 0.0015 mol per mol of silver |

Seventh Layer: Second Green-Sensitive Emulsion Layer (GL$_2$)
A silver iodobromide emulsion (iodide content: 5 mol %)

| | silver coated amount: 1.6 g/m$^2$ |
|---|---|
| Sensitizing Dye III | $2.5 \times 10^{-5}$ mol per mol of silver |
| Sensitizing Dye IV | $0.8 \times 10^{-5}$ mol per mol of silver |
| Coupler B | 0.02 mol per mol of silver |
| Coupler M-1 | 0.003 mol per mol of silver |
| Coupler (16) | 0.0003 mol per mol of silver |

Eighth Layer: Yellow Filter Layer (YEL)
A gelatin layer containing yellow colloidal silver and a dispersion of 2,5-di-tert-octylhydroquinone
Ninth Layer: First Blue-Sensitive Emulsion Layer (BL$_1$)
A silver iodobromide emulsion (iodide content: 6 mol %)

| | silver coated amount: 1.5 g/m$^2$ |
|---|---|
| Coupler Y-1 | 0.25 mol per mol of silver |

Tenth Layer: Second Blue-Sensitive Emulsion Layer (BL$_2$)
A silver iodobromide emulsion (iodide content: 6 mol %)

| | silver coated amount: 1.1 g/m$^2$ |
|---|---|
| Coupler Y-1 | 0.06 mol per mol of silver |

Eleventh Layer: Protective Layer (PL)
A gelatin layer containing polymethyl methacrylate particles (having a diameter of about 1.5 microns)
---

A gelatin hardener and a surface active agent were incorporated into each of the layers in addition to the above described components.

The thus-prepared sample was designated Sample 101.

Sample 102

Sample 102 was prepared in the same manner as Sample 101 except that Coupler (38) was used in place of Coupler (16) in RL$_1$ and RL$_2$ in an amount same as in Sample 101 and Coupler (5) was used in place of Coupler (16) in GL$_1$ and GL$_2$ in an amount of twice of Coupler (16).

Sample 103

Sample 103 was prepared in the same manner as Sample 101 except that DIR Coupler D-1 was used in place of Coupler (16) in an amount same as in Sample 101.

Sample 104

Sample 104 was prepared in the same manner as Sample 101 except that DIR Coupler D-2 was used in place of Coupler (16) in an amount same as in Sample 101.

Sample 105

Sample 105 was prepared in the same manner as Sample 101 except that DIR Coupler D-3 was used in place of Coupler (16) in an amount same as in Sample 101.

Comparison DIR Coupler D-1:

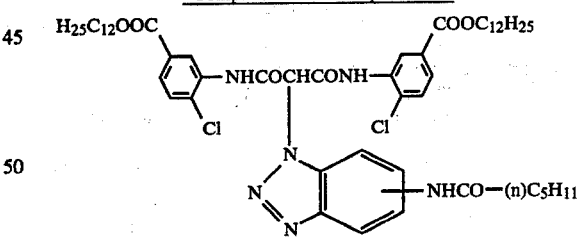

Comparison DIR Coupler D-2:

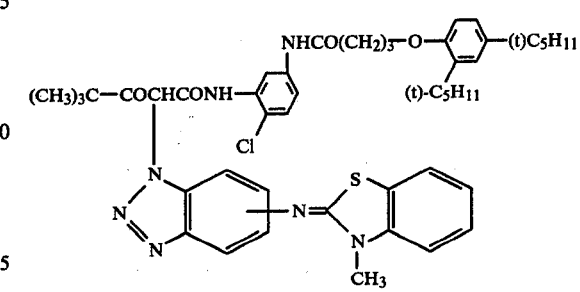

Comparison DIR Coupler D-3:

-continued

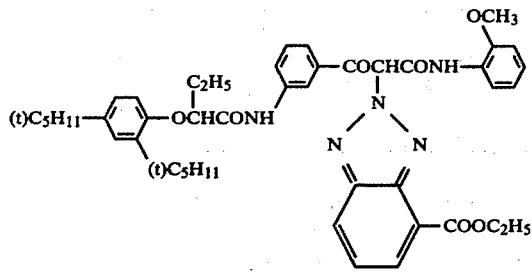

The compounds used for the preparation of the above-described samples were:

Sensitizing Dye I

Pyridinium salt of anhydro-5,5'-dichloro-3,3'-di(γ-sulfopropyl)-9-ethylthiacarbocyanine hydroxide

Sensitizing Dye II

Triethylamine salt of anhydro-9-ethyl-3,3'-di(γ-sulfopropyl)-4,5,4',5'-dibenzothiacarbocyanine hydroxide

Sensitizing Dye III

Sodium salt of anhydro-9-ethyl-5,5'-dichloro-3,3'-di(γ-sulfopropyl)oxacarbocyanine

Sensitizing Dye IV

Sodium salt of anhydro-5,6,5',6'-tetrachloro-1,1'-diethyl-3,3'-di{β-[β-(γ-sulfopropoxy)ethoxy]ethyl}imidazolocarbocyanine hydroxide Coupler A:

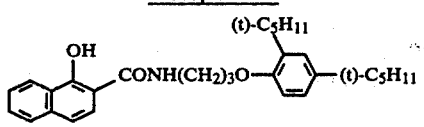

Coupler B:

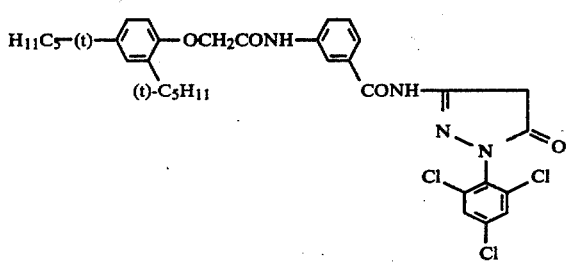

Coupler C-1:

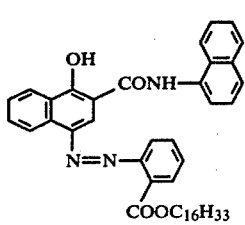

Coupler C-2:

-continued

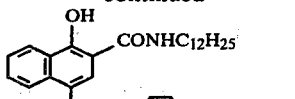

Coupler C-3:

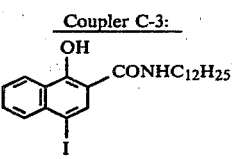

Coupler M-1:

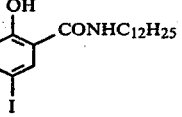

Coupler Y-1:

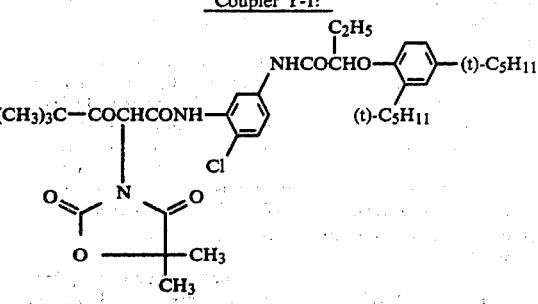

Samples 101 to 105 thus obtained were cut into films of 35 mm size and 600 m in length, exposed using a step wedge, and subjected to the following development processing.

1. Color Development—3 min 15 sec
2. Bleaching—6 min 30 sec
3. Washing—3 min 15 sec
4. Fixing—6 min 30 sec
5. Washing—3 min 15 sec
6. Stabilizing—3 min 15 sec The processing solutions used in the above steps had the following compositions:

| Color Developing Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N—Ethyl-N—β-hydroxyethylamino)-2-methylaniline Sulfate | 4.5 g |
| Water to make | 1 l |
| Bleaching Solution | |
| Ammonium Bromide | 160.0 g |
| Ammonia (28% aq. soln.) | 25.0 ml |
| Sodium Ferric Ethylenediaminetetraacetate | 130.0 g |
| Glacial Acetic Acid | 14.0 ml |
| Water to make | 1 l |
| Fixing Solution | |
| Sodium Tetrapolyphosphate | 2.0 g |
| Sodium Sulfite | 4.0 g |

| -continued | |
|---|---|
| Ammonium Thiosulfate (70% aq. soln.) | 175.0 ml |
| Sodium Bisulfite | 4.6 g |
| Water to make | 1 l |
| Stabilizing Solution | |
| Formalin | 8.0 ml |
| Water to make | 1 l |

Further, an overflow portion of the developing solution was repeatedly used after being subjected to regeneration treatment in the following manner.

The regeneration treatment was carried out in a batch type process. The overflow liquid was put into a container for electrodialysis and electrodialyzed so as to make a concentration of potassium bromide not more than 0.7 g per liter. To the liquid were added sodium nitrilotriacetate, sodium sulfite, sodium carbonate, potassium bromide, hydroxylamine sulfate and 4-(N-ethyl-N-β-hydroxyethylamino)-2-methylaniline sulfate which had been consumed during the running of operation and pH of the liquid was adjusted to 10.05. The liquid was reused as a replenisher.

The operation was run under conditions of treating light-sensitive material at a rate of 0.1 m²/min with replenishing processing liquid in an amount of 1.3 l/m². Each time when the overflow liquid amounted to 1 l the above consumed components were replenished to form a replenisher. This procedure was repeated 10 times.

The decrease in sensitivity after 10 times of reuse as stated above was determined and the results are shown in Table 1 below. From the results shown in Table 1, it is apparent that the decrease in sensitivity is hardly observed with Samples 101 and 102, on the contrary, a remarkable decrease in sensitivity is observed with Samples 103, 104 and 105. This fact indicates that when the releasing groups of Couplers (5), (16) and (38) are diffused out into a color developing solution, they are decomposed to the compounds which are photographically non-effective and are not accumulated in the color developing solution being different from other non-decomposable releasing groups. Therefore, the color developing solution is capable of being used repeatedly.

TABLE 1

| | Δ S fog + 0.3* | | |
|---|---|---|---|
| Sample No. | B | G | R |
| 101 | +0.02 | ±0 | ±0 |
| 102 | +0.02 | −0.02 | ±0 |
| 103 | −0.20 | −0.12 | −0.05 |
| 104 | −0.15 | −0.03 | ±0 |
| 105 | −0.12 | −0.07 | ±R |

*The decrease in sensitivity at a density of fog + 0.3 indicated in log E unit.

EXAMPLE 2

Sample 201

Sample 201 was prepared in the same manner as Sample 101 except that Coupler (18) was used in place of Coupler (16) in an amount of 1.2 times of Coupler (16).

Sample 202

Sample 202 was prepared in the same manner as Sample 101 except that Coupler (15) was used in place of Coupler (16) in an amount of 2 times of Coupler (16).

Sample 203

Sample 203 was prepared in the same manner as Sample 101 except that DIR Coupler D-4 was used in place of Coupler (16) in an amount same as in Sample 101.

Comparison DIR Coupler D-4:

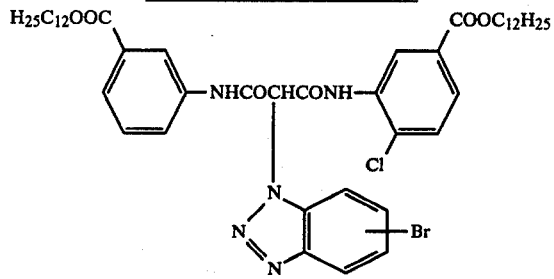

Samples 201 to 203 were cut into films of 35 mm size and 100 m in length, exposed using a wedge and subjected to a development processing as shown in Example 1 using a 5-liter tank of the developing solution. The sensitivity at the first portion of the sample thus processed and that of the last portion of the sample are compared and the decrease in the sensitivity of the latter is shown in Table 2 below.

From the results shown in Table 2, it is apparent that the decrease in sensitivity is small with Samples 201 and 202 in comparison with Sample 203. This indicates that the releasing groups of Couplers (15) and (18) are decomposed to the compounds which are substantially photographically non-effective after they diffused into the color developing solution.

TABLE 2

| | Δ S fog + 0.3* | | |
|---|---|---|---|
| Sample No. | B | G | R |
| 201 | −0.02 | ±0 | ±0 |
| 202 | −0.02 | ±0 | ±0 |
| 203 | −0.13 | −0.10 | −0.05 |

*The decrease in sensitivity at a density of fog + 0.3 indicated in log E unit.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a silver halide emulsion layer containing a coupler having, at the coupling active position, a group which provides a compound having a development inhibiting property when the group is released from the coupling active position of the coupler upon the color development reaction and which is decomposed to a compound which does not substantially influence the photographic properties when the compound diffuses into a color developing solution, the coupler containing no water-soluble group during development but becoming water-soluble when dissolved in a developer and hydrolyzed and the coupler being represented by general formula (I)

$$A-L_1)_aZ-L_2-Y)_b \qquad (I)$$

wherein A represents a coupler component; Z represents an essential portion of a compound having a development inhibiting function which is bonded to the coupling position of the coupler directly (when a is 0) or through a connecting group of the formula $L_1$ (when a is 1), the portion being represented by any one of the formulae

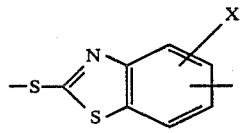

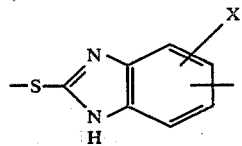

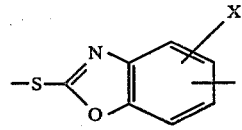

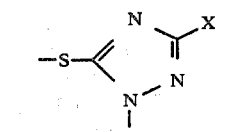

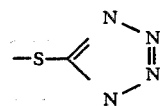

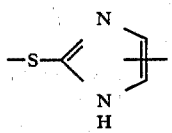

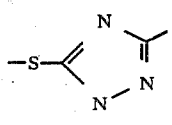

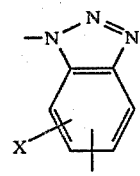

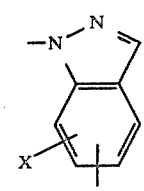

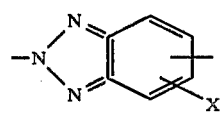

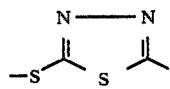

where X represents a hydrogen atom, a halogen atom, an alkyl group, an alkenyl group, an alkanamido group, an alkenamido group, an alkoxy group, a sulfonamido group, or an aryl group; Y represents a substituted straight chain or substituted branch chain alkyl group, a cyclic alkyl group which is unsubstituted or substituted, an alkenyl group, an aryl group, an aralkyl group or a heterocyclic group; $L_1$ represents

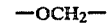

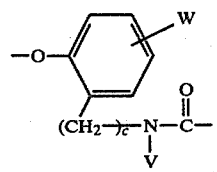

where V represents a hydrogen atom or an alkyl group having 1 to 10 carbon atoms, W represents a hydrogen atom, a halogen atom, an alkyl group having from 1 to 10 carbon atoms, an alkanamido group having from 1 to 10 carbon atoms, an alkoxy group having from 1 to 10 carbon atoms, an alkoxycarbonyl group having from 1 to 10 carbon atoms, an aryloxycarbonyl group, an alkanesulfonamido group having from 1 to 10 carbon atoms, an aryl group, a carbamoyl group, an N-alkylcarbamoyl group having from 1 to 10 carbon atoms, a nitro group, a cyano group, an arylsulfonamido group, a sulfamoyl group, or an imido group, and c is 0 or an integer of 1 or 2; $L_2$ is a divalent connecting group containing a chemical bond which is broken in a photographic developing solution, the chemical bond being represented by the formula

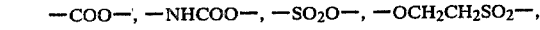

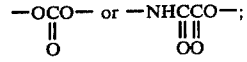

a represents 0 or 1; and b represents 1 or 2, and when b is 2, the groups represented by $-L_2-Y$ may be the same or different.

2. A silver halide color photographic light-sensitive material as in claim 1, wherein said divalent connecting group is connected on one side to Z directly or through an alkylene group and/or a phenylene group, and on the other side to Y directly, provided that when said chemical bond is connected to Z through an alkylene group or a phenylene group, said alkylene group or said phenylene group may contain an ether bond, an amido bond, a carbonyl group, a thioether bond, a sulfone group, a sulfonamido bond and a urea bond.

3. A silver halide color photographic light-sensitive material as in claim 2, wherein the residue represented by the formula $-Z-L_2-Y)_b$ is represented by the formulae

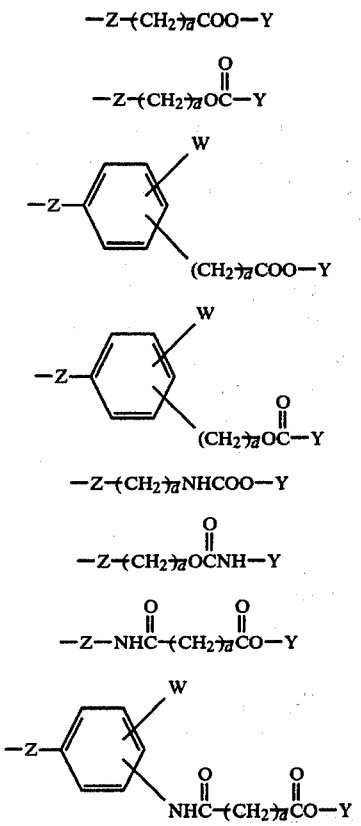

wherein Z and Y each has the same meaning as defined above; d represents 0 or an integer of 1 to 10; and W represents a hydrogen atom, a halogen atom, an alkyl group having from 1 to 10 carbon atoms, an alkanamido group having from 1 to 10 carbon atoms, an alkoxy group having from 1 to 10 carbon atoms, an alkoxycarbonyl group having from 1 to 10 carbon atoms, an aryloxycarbonyl group, an alkanesulfonamido group having from 1 to 10 carbon atoms, an aryl group, a carbamoyl group, an N-alkylcarbamoyl group having from 1 to 10 carbon atoms, a nitro group, a cyano group, an arylsulfonamido group, a sulfamoyl group, or an imido group.

4. A silver halide color photographic light-sensitive material as in claim 1, wherein A is a yellow color image forming coupler residue of a pivaloylacetanilide type, a benzoylacetanilide type, a malondiester type, a malondiamide type, a dibenzoylmethane type, a benzothiazolylacetamide type, a malonester monoamide type, a benzothiazolylacetate type, a benzoxazolylacetamide type, a benzoxazolylacetate type, a malondiester type, a benzimidazolylacetamide type, or a benzimidazolylacetate type.

5. A silver halide color photographic light-sensitive material as in claim 1, wherein A is a magenta color image forming coupler residue having 5-oxo-2-pyrazoline nucleus or a pyrazolo[1,5-a]benzimidazole nucleus.

6. A silver halide color photographic light-sensitive material as in claim 1, wherein A is a cyan color image forming coupler residue having a phenol nucleus or an α-naphthol nucleus.

7. A silver halide color photographic light-sensitive material as in claim 1, wherein A is a non-color-forming coupler residue.

8. A silver halide color photographic light-sensitive material as in claim 1, wherein the essential portion of a development inhibitor represented by Z is a divalent heterocyclic group or a divalent heterocyclic thio group.

9. A silver halide color photographic light-sensitive material as in claim 1, wherein the alkyl group represented by X is a straight chain, branched chain, or cyclic alkyl group having from 1 to 10 carbon atoms.

10. A silver halide color photographic light-sensitive material as in claim 1, wherein the alkanamido group represented by X is a straight chain, branched chain or cyclic alkanamido group having 1 to 10 carbon atoms.

11. A silver halide color photographic light-sensitive material as in claim 1, wherein the alkoxy group represented by X is a straight chain, branched chain, or cyclic alkoxy group having from 1 to 10 carbon atoms.

12. A silver halide color photographic light-sensitive material as in claim 1, wherein the alkyl group represented by Y is a straight chain or branched chain alkyl group having 1 to 10 carbon atoms which is substituted or a cyclic alkyl group having 3 to 10 carbon atoms which may be substituted.

13. A silver halide color photographic light-sensitive material as in claim 1, wherein the alkyl group, the alkenyl group, the alkanamido group, the alkenamido group or the alkoxy group represented by X or the alkyl group or the alkenyl group represented by Y is substituted with a halogen atom, a nitro group, an alkoxy group having from 1 to 4 carbon atoms, an aryloxy group having from 6 to 10 carbon atoms, an alkanesulfonyl group having from 1 to 4 carbon atoms, an arylsulfonyl group having from 6 to 10 carbon atoms, an alkanamido group having from 1 to 5 carbon atoms, an anilino group, a benzamido group, an alkylcarbamoyl group having from 1 to 6 carbon atoms, a carbamoyl group, an arylcarbamoyl group having from 6 to 10 carbon atoms, an alkylsulfonamido group having 1 to 4 carbon atoms, an arylsulfonamido group having from 6 to 10 carbon atoms, an alkylthio group having from 1 to 4 carbon atoms, an arylthio group having from 6 to 10 carbon atoms, a phthalimido group, a succinimido group, an imidazolyl group, a 1,2,4-triazolyl group, a pyrazolyl group, a benzotriazolyl group, a furyl group, a benzothiazolyl group, an alkylamino group having from 1 to 4 carbon atoms, an alkanoyl group having from 1 to 4 carbon atoms, a benzoyl group, an alkanoyloxy group having from 1 to 4 carbon atoms, a benzoyloxy group, a perfluoroalkyl group having from 1 to 4 carbon atoms, a cyano group, a tetrazolyl group, a hydroxy group, a carboxy group, a mercapto group, a sulfo group, an amino group, an alkylsulfamoyl group having from 1 to 4 carbon atoms, an arylsulfamoyl group having from 6 to 10 carbon atoms, a morpholino group, an aryl group having from 6 to 10 carbon atoms, a pyrrolidinyl group, a ureido group, a urethane group, an alkoxycarbonyl group having from 1 to 6 carbon atoms, an aryloxycarbonyl group having from 6 to 10 carbon atoms, an imidazolidinyl group, or an alkylidenamino group having from 1 to 6 carbon atoms.

14. A silver halide color photographic light-sensitive material as in claim 1, wherein the aryl group represented by Y is substituted with halogen atom, a nitro group, an alkyl group having from 1 to 4 carbon atoms, an alkoxy group having from 1 to 4 carbon atoms, an aryloxy group having from 6 to 10 carbon atoms, an alkanesulfonyl group having from 1 to 4 carbon atoms, an arylsulfonyl group having from 6 to 10 carbon atoms, an alkanamido group having 1 to 5 carbon atoms, an anilino group, a benzamido group, an alkylcarbamoyl group having from 1 to 6 carbon atoms, a carbamoyl group, an arylcarbamoyl group having from 6 to 10 carbon atoms, an alkylsulfonamido group having 1 to 4 carbon atoms, an arylsulfonamido group having from 6 to 10 carbon atoms, an alkylthio group having from 1 to 4 carbon atoms, an arylthio group having from 6 to 10 carbon atoms, a phthalimido group, a succinimido group, an imidazolyl group, a 1,2,4-triazolyl group, a pyrazolyl group, a benzotriazolyl group, a furyl group, a benzothiazolyl group, an alkylamino group having from 1 to 4 carbon atoms, an alkanoyl group having from 1 to 4 carbon atoms, a benzoyl group, an alkanoyloxy group having from 1 to 4 carbon atoms, a benzoyloxy group, a perfluoroalkyl group having from 1 to 4 carbon atoms, a cyano group, a tetrazolyl group, a hydroxy group, a carboxy group, a mercapto group, a sulfo group, an amino group, an alkylsulfamoyl group having from 1 to 4 carbon atoms, an arylsulfamoyl group having from 6 to 10 carbon atoms, a morpholino group, an aryl group having from 6 to 10 carbon atoms, a pyrrolidinyl group, a ureido group, a urethane group, an alkoxycarbonyl group having from 1 to 6 carbon atoms, an aryloxycarbonyl group having from 6 to 10 carbon atoms, an imidazolidinyl group, or an alkylidenamino group having from 1 to 6 carbon atoms.

15. A silver halide color photographic light-sensitive material as in claim 1, wherein the aryl group represented by Y is a phenyl group or a napththyl group.

16. A silver halide color photographic light-sensitive material as in claim 1, wherein the heterocyclic group represented by Y is a diazolyl group, a triazolyl group, a thiazolyl group, an oxazolyl group, a pyrrolyl group, a pyridyl group, a diazinyl group, a triazinyl group, a furyl group, a diazolinyl group, a pyrrolinyl group, or a thienyl group.

17. A silver halide color photographic light-sensitive material as in claim 1, wherein said coupler is represented by formula (II), (III), or (IV)

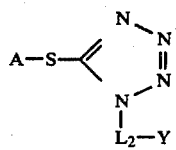
(II)

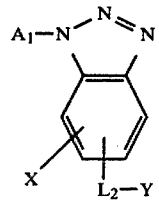
(III)

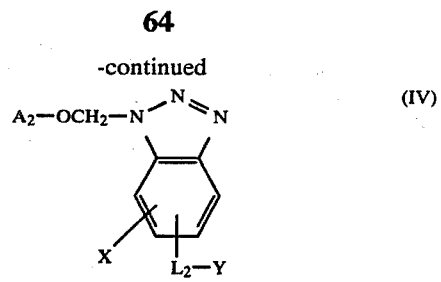
(IV)

wherein A, $L_2$, and Y each has the same meanings as defined for formula (I); $A_1$ represents a yellow coupler residue, a magenta coupler residue or substantially non-color forming coupler residue same as defined for formula (I); X represents a hydrogen atom, a halogen atom, an alkyl group, an alkenyl group, an alkanamido group, an alkenamido group, an alkoxy group, a sulfonamido group, or an aryl group; and $A_2$ represents a cyan coupler residue as defined for formula (I).

18. A silver halide color photographic light-sensitive material as in claim 17, wherein said coupler is represented by formula (V) or (VI)

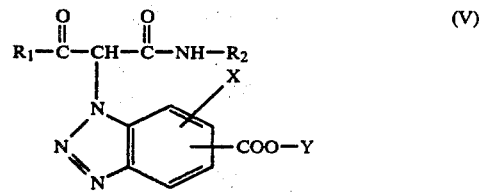
(V)

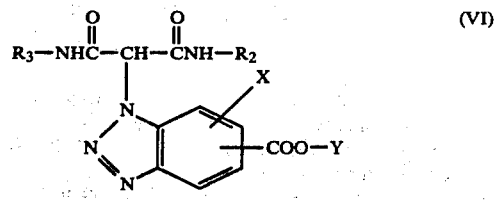
(VI)

wherein $R_1$ represents an aliphatic group, an aromatic group, an alkoxy group, or a heterocyclic group, and $R_2$ and $R_3$ each represents an aromatic group or a heterocyclic group, and each of said groups represented by $R_1$, $R_2$, and $R_3$ may be substituted; and X and Y each has the same meaning as defined for formula (III).

19. A silver halide color photographic light-sensitive material as in claim 17, wherein said coupler is represented by formula (VII) or (VIII)

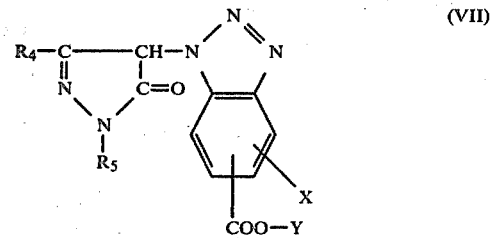
(VII)

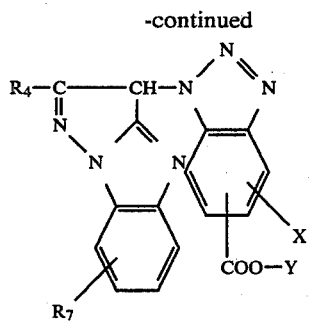

(VIII)

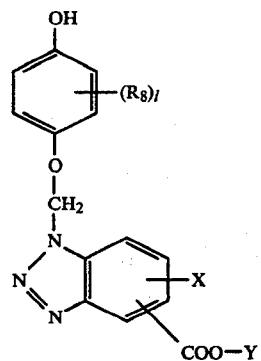

(IX)

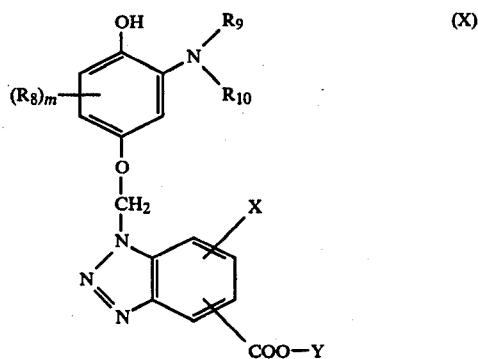

(X)

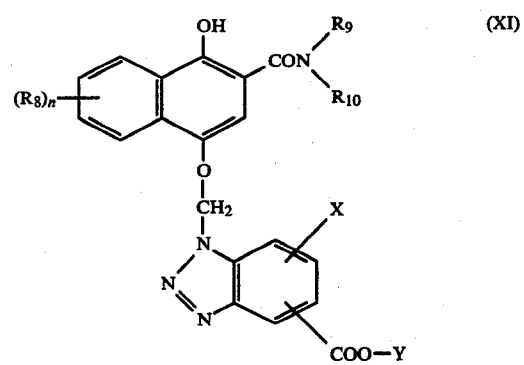

(XI)

wherein $R_4$ represents a hydrogen atom, an alkyl group, an alkenyl group, a cyclic alkyl group, an aralkyl group, a cyclic alkenyl group, an aryl group, a heterocyclic group, an alkoxycarbonyl group, an aryloxycarbonyl group, an aralkyloxycarbonyl group, an alkoxy group, an aryloxy group, an alkylthio group, an arylthio group, a carboxy group, an acylamino group, a diacylamino group, an N-alkylacylamino group, an N-arylacylamino group, a ureido group, a urethane group, a thiourethane group, an arylamino group, an alkylamino group, a cycloamino group, a heterocylcic amino group, an alkylcarbonyl group, an arylcarbonyl group, a sulfonamido group, a carbamoyl group, a sulfamoyl group, a cyano group, a hydroxy group, a marcapto group, a halogen atom, or a sulfo group; $R_5$ represents an alkyl group, an alkenyl group, a cyclic alkyl group, an aralkyl group, a cyclic alkenyl group, an aryl group, a heterocyclic group, an aliphatic acyl group, an aromatic acyl group, an alkylsulfonyl group, an arylsulfonyl group, an alkylcarbamoyl group, an arylcarbamoyl group, an alkylthiocarbamoyl group, or an arylthiocarbamoyl group; $R_7$ represents a hydrogen atom, an alkyl group, an alkenyl group, a cyclic alkyl group, an aralkyl group, a cyclic alkenyl group, an aryl group, a heterocyclic group, a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamide group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group, or a mercapto group; and X and Y each has the same meaning as defined for formula (III).

20. A silver halide color photographic light-sensitive material as in claim 17, wherein said coupler is represented by formula (IX), (X), or (XI)

wherein $R_8$ represents a hydrogen atom, a halogen atom, an aliphatic hydrocarbon residue, an acylamino group, a group having the formula $-O-R_{11}$ or the formula $-S-R_{11}$ wherein $R_{11}$ represents an aliphatic hydrocarbon residue, and when two or more $R_8$ are present in one molecule, the $R_8$ groups may be the same or different; $R_9$ and $R_{10}$ each represents an aliphatic hydrocarbon residue, an aryl group or a heterocyclic group, one of $R_9$ and $R_{10}$ may be a hydrogen atom, or $R_9$ and $R_{10}$ may combine with each other to form a nitrogen-containing heterocyclic nucleus; l represents an integer of 1 to 4; m represents an integer of 1 to 3, and n represents an integer of 1 to 5.

21. A silver halide color photographic light-sensitive material as in claim 1, wherein the concentration of said coupler is 0.01 to 50 mols per mol of silver halide.

22. A silver halide color photographic light-sensitive material as in claim 1, wherein the concentration of said coupler is 0.1 to 5 mols per mol of silver halide.

* * * * *